(12) United States Patent
Murugesan et al.

(10) Patent No.: US 7,754,755 B2
(45) Date of Patent: Jul. 13, 2010

(54) INHIBITORS OF 15-LIPOXYGENASE

(75) Inventors: Natesan Murugesan, Princeton Junction, NJ (US); John E. Macor, Guilford, CT (US); Zhengxiang Gu, Princeton, NJ (US); Leena Fadnis, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 208 days.

(21) Appl. No.: 11/231,729

(22) Filed: Sep. 21, 2005

(65) Prior Publication Data

US 2006/0063823 A1 Mar. 23, 2006

Related U.S. Application Data

(60) Provisional application No. 60/612,464, filed on Sep. 23, 2004.

(51) Int. Cl.
| | |
|---|---|
| A61K 31/405 | (2006.01) |
| A61K 31/38 | (2006.01) |
| A61K 31/34 | (2006.01) |
| A61K 31/28 | (2006.01) |
| C07D 209/10 | (2006.01) |
| C07D 409/12 | (2006.01) |
| C07D 307/91 | (2006.01) |
| C07D 307/00 | (2006.01) |

(52) U.S. Cl. .................. 514/415; 514/444; 514/468; 514/498; 548/507; 549/59; 549/460; 549/467

(58) Field of Classification Search .............. 548/507; 514/415, 444, 468, 498; 549/59, 460, 467
See application file for complete search history.

(56) References Cited

U.S. PATENT DOCUMENTS

| | | | | |
|---|---|---|---|---|
| 4,774,240 | A * | 9/1988 | Boshagen et al. | 514/228.2 |
| 5,612,359 | A | 3/1997 | Murugesan | |
| 5,712,279 | A | 1/1998 | Biller et al. | |
| 5,739,135 | A | 4/1998 | Biller et al. | |
| 5,760,246 | A | 6/1998 | Biller et al. | |
| 6,043,265 | A | 3/2000 | Murugesan et al. | |
| 6,548,529 | B1 | 4/2003 | Robl et al. | |
| 6,706,720 | B2 | 3/2004 | Atwal et al. | |

FOREIGN PATENT DOCUMENTS

WO WO 00/01389 1/2000

OTHER PUBLICATIONS

Ho et al. "Hydroxyindole-O-methyltransferase VI: Inhibitory Activities of Substituted Benzoyltrytamines and Benzenesulfonyltryptamines" Journal of Pharmaceutical Sciences, 1971, vol. 60, No. 4, pp. 636-637.*

Bailey et al. "Further Examination of the Reactions of Simple Indoles with Arenesulphoneyl Azides" Journal of the Chemical Society, Perkin Transactions I, 1973, 1602-1606.*

Shono et al. CAS Accession No. 1983:487977.*

Bleich, D. et al., "Resistance to type 1 diabetes induction in 12-lipoxygenase knockout mice.", The Journal of Clinical Investigation, vol. 103, No. 10, pp. 1431-1436 (1999).

Bocan, T. et al., "A specific 15-lipoxygenase inhibitor limits the progression and monocyte-macrophage enrichment of hypercholesterolemia-induced atherosclerosis in the rabbit", Atherosclerosis, vol. 136, pp. 203-216 (1998).

Gan, Qing-Fen et al., "Defining the Arachidonic Acid Binding Site of Human 15-Lipoxygenase", The Journal of Biological Chemistry, vol. 271, No. 41, pp. 25412-25418 (1996).

Jiang, Zhen-Yue et al., "Lipid Hydroperoxide Measurement by Oxidation of $Fe^{2+}$ in the Presence of Xylenol Orange. Comparison with the TBA Assay and an Iodometric Method", LIPIDS, vol. 26, No. 10, pp. 853-856 (1991).

Kelavkar,U. et al., "The Effect of 15-Lipoxygenase-1 Expression on Cancer Cells", Current Urology Reports, vol. 3, pp. 207-214 (2002).

Rapoport, S. et al., "The Lipoxygenase of Reticulocytes", Eur. J. Biochem., vol. 96, pp. 545-561 (1979).

Setty, B.N. et al., "15-Hydroxyeicosatetraenoic Acid-Mediated Potentiation of Thrombin-Induced Platelet Functions Occurs via Enhanced Production of Phosphoinositide-Derived Second Messengers-sn-1,2-Diacylglycerol and Inosito-1,4,5-Trisphosphate", Blood, vol. 80, No. 11, pp. 2765-2773 (1992).

Sultana, C. et al., "Lipoxygenase Metabolites Induced Expression of Adhesion Molecules and Transendothelial Migration of Monocyte-Like HL-60 Cells is Linked to Protein Kinase C Activation", Journal of Cellular Physiology, vol. 167, pp. 477-487 (1996).

Tisdale, Michael J., "Protein Loss in Cancer Cachexia", Science, vol. 289, pp. 2293-2294 (2000).

Database CHEMCATS on STN, AN 2005:1497030. Interchim Intermediates Benzenesulfonamide, N-[2-(1H-indol-3-yl)ethyl]-2,3,4,5,6-pentamethyl- Jan. 18, 2005.

* cited by examiner

Primary Examiner—Joseph R Kosack
(74) Attorney, Agent, or Firm—Hong Liu

(57) ABSTRACT

The present invention provides inhibitors of 15-LO according to Formula I, pharmaceutical compositions containing such inhibitors and methods for treating diseases related to the 15-LO cascade using such compounds and compositions.

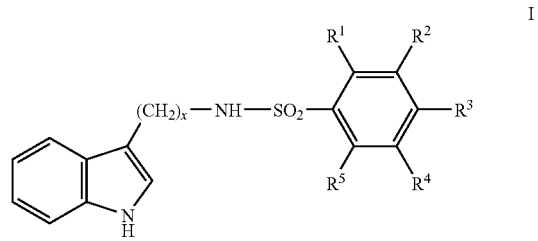

2 Claims, No Drawings

INHIBITORS OF 15-LIPOXYGENASE

RELATED APPLICATIONS

This application claims priority benefit under Title 35 §119 (e) of U.S. Provisional Application No. 60/612,464, filed Sep. 23, 2004, the contents of which are herein incorporated by reference.

FIELD OF THE INVENTION

The present invention relates to inhibitors of the enzyme 15-lipoxygenase ("15-LO"), pharmaceutical compositions comprising said inhibitors, and methods of treating diseases responsive to inhibition of 15-lipoxygenase.

BACKGROUND OF THE INVENTION

The 15-LO cascade is implicated in various inflammatory disorders, including disorders involving the origin and recruitment of foam cells. Cholesterol is transported in blood particles called lipoproteins, which include low-density lipoproteins (LDL). Lipoproteins contain cholesterol and are necessary for foam cell formation. The formation of foam cells can lead to serious disorders. For example, hypercholesterolemia can induce monocytes to migrate into the arterial wall and mature into foam cells or tissue macrophages that accumulate fatty material, including cholesterol esters. Continued creation of foam cells thickens the inner lining of medium and large arteries, thereby forming atherosclerotic plaques or lesions containing cholesterol, smooth muscle cells, and connective tissue cells. Affected arteries lose elasticity and become narrowed or obstructed by the plaques indicating the onset of atherosclerosis. Atherosclerotic plaques may collect calcium, become brittle, and even rupture triggers the formation of a blood clot or thrombus capable of occluding an artery and causing a stroke or heart attack. In addition to atherosclerosis, hypercholesteremia plays a role in peripheral vascular diseases of small arteries, veins and lymphatics. Thus, hypercholesteremia may also affect the arms, legs, kidneys and other vital organs in addition to the heart and brain.

Lipoxygenases are enzymes that catalyze the oxidation of polyunsaturated fatty acids and esters thereof, including those found in low-density lipoproteins. In addition to metabolism of free fatty acids, the enzyme 15-lipoxygenase (15-LO) also oxidizes esterified polyenoic fatty acids. Related to its general pathology, it is believed that oxidative metabolites of the 15-LO cascade [e.g. the arachidonic acid metabolite 15-hydroperoxyeicosatetraenoic acid (15-HPETE)], induce endothelial cell activation and subsequent adhesion molecule expression resulting in monocyte recruitment to the vessel wall [Sultana et al, J. of Cellular Physiology 167 (1996) 467-487]. 15-Hydroxyeicosatetraenoic acid (15-HETE), a reduction product of 15-HPETE, has also been implicated in the potentiation of thrombin-induced platelet activation [Setty et al, Blood, 80:11 (1992): 2765-2773]. It has also been demonstrated that arachidonic acid metabolites of the 15-LO cascade, namely 15-hydroperoxyeicosatetraenoic acid (15-HPETE), induce a pro-thrombotic state in endothelial cells through enhancement of plasminogen activator inhibitor-1 (PAI-1) release. Additionally, evidence that 15-LO is involved in the pathology of diabetes, it has been demonstrated that deletion of the mouse gene homologue of 15-LO leads to a reduction of disease progression [Bleich et al, J Clin Invest (1999) May 15; 103(10):1431-6]. 15-LO has also been implicated in the progression of various cancers [Kelavkar et al, Curr Urol Rep 2002 June; 3(3):207-14]. Not only in the progression of the cancer itself, but also in its related pathologies including cachexia and wasting [Tisdale et al, Science 2000 Sep. 29; 289(5488):2293-4].

Inhibition of 15-LO, therefore, would be useful to prevent and treat diseases with either an inflammatory component, a thrombotic component, or both as in the case of atherosclerosis, as well as various cancers. For example, it has been shown that treatment with a 15-LO inhibitor suppressed atherogenesis (or the production of atheroma—a fatty degeneration of the arterial wall) in rabbits fed a high-fat diet [Bocan et al, Atherosclerosis, 136 (1998): 203-216]. Additional diseases in which treatment with a 15-LO inhibitor would be useful include asthma, psoriasis, osteoarthritis, rheumatoid arthritis, Alzheimer's disease, and chronic obstructive pulmonary disease.

SUMMARY OF THE INVENTION

The present invention provides inhibitors of 15-LO, pharmaceutical compositions containing such inhibitors, and methods for treating diseases related to the 15-LO cascade using such compounds and compositions. In a first embodiment, the present invention provides compounds of Formula I:

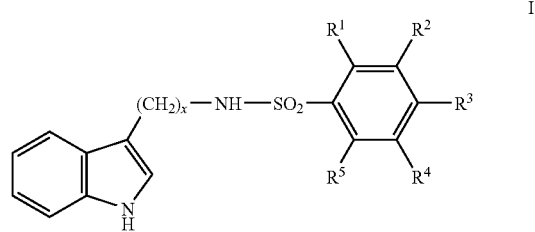

including enantiomers, diastereomers, salts and solvates thereof, wherein:

$R^1$, $R^2$, $R^3$, $R^4$ and $R^5$ are independently selected from the group consisting of hydroxy, alkyl, alkenyl, alkynyl, oxyalkyl, oxyalkenyl, oxyalkynyl, oxyaryl, oxyperfluoroalkyl, thioalkyl, thioalkenyl, thioalkynyl, thioaryl, thioheteroaryl, thiocycloalkyl, aryl, heteroaryl, heterocyclyl, amino, nitrile, nitro, halogen, alkylcarbo, aminocarboalkyl, aminocarboalkenyl, aminocarboalkynyl, aminocarboaryl, aminocarbocycloalkyl, aminocarboheterocyclyl, aminocarboheteroaryl, perfluoroalkyl, perfluoroalkenyl, perfluoroalkynyl, carboxyalkyl, carboxyalkenyl, carboxyalkynyl, carboxyaryl, carboxyheteroaryl, carboxycycloalkyl, and cycloalkyl, wherein each aryl and oxyaryl may optionally be substituted with one or more carbohydroxy, carboaminoaryl, carboaminoalkylaryl and alkylaryl;

x is 2, 3 or 4.

A first preferred embodiment of the present invention provides compounds according to Formula I, wherein:

$R^1$, $R^2$, $R^3$, $R^4$ and $R^5$ are independently selected from the group consisting of alkyl, oxyalkyl, oxyperfluoroalkyl, thioalkyl, aryl, nitrile, nitro, halogen, alkylcarbo, aminocarboalkyl, perfluoroalkyl, carboxyalkyl, and cycloalkyl, wherein each aryl may optionally be substituted with one or more carbohydroxy, carboaminoaryl, carboaminoalkylaryl and alkylaryl.

Further, in a second embodiment, the present invention provides a novel pharmaceutical composition, comprising a compound according to Formula I and a pharmaceutically acceptable adjuvant or carrier.

Finally, in a third embodiment, the present invention provides a method for treating a 15-lipoxygenase mediated disease or disorder, comprising: administering to a mammal in need of treatment a therapeutically effective amount of a compound according to Formula I.

In a second preferred embodiment, the present invention provides methods for treating a 15-lipoxygenase mediated disease or disorder, wherein the 15-lipoxygenase mediated disease or disorder is selected from the group consisting of inflammatory disorder, atherosclerosis, formation of atherosclerotic plaques, thrombosis, peripheral arterial disease, coagulation syndromes, intermittent claudication, diabetes, vascular restenosis, hypertension, asthma, rheumatoid arthritis, osteoarthritis, cancer and inflammatory bowel disease.

In a third preferred embodiment, the present invention provides methods for treating inflammatory disorders, wherein the inflammatory disorder involves the origin and recruitment of foam cells.

DETAILED DESCRIPTION OF THE INVENTION

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

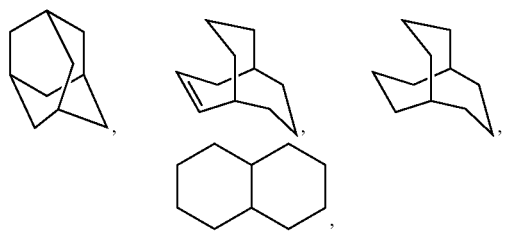

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, alkenyl, alyalkynyl, oxyperfluoroalkyl (e.g. —$OCF_3$), oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl.

The term "carbo" as used herein as part of another group refers to a carbonyl (C=O) group serving as a linker between two groups such as, for example, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl and thiocycloalkyl.

The term "perfluoro" as used herein as part of another group refers to a group wherein more than one hydrogen atom attached to one or more carbon atoms in the group has been replaced with a fluorine atom such as, for example, perfluoroalkyl (e.g. —$CF_3$), perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfo" as used herein as part of another group refers to an —$SO_2$— group such as, for example, sulfalkyl, sulfoalkenyl, sulfoalkynyl, sulfoaryl, sulfocycloalkyl, sulfoheterocyclyl and sulfoheteroaryl.

The term "nitro" as used herein alone or as part of another group refers to an —$NO_2$ group.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch 5, pgs 113-191 (Harwood Academic Publishers, 1991). Said references are incorporated herein by reference.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Purification by Cation Exchange Chromotography

Cation exchange chromatography was performed on Worldwide Monitoring clean-up CUBCX1HL2M6 cartridges. The cartridge was loaded with a dichloromethane solution of crude product. The resin was eluted with dichloromethane and the appropriate fractions were combined and evaporated to give the product.

Purification by Reverse-Phase Preparative HPLC

Reverse-phase preparative HPLC was performed with Shimadzu 8A liquid chromatographs using YMC S5 ODS columns (20×100, 20×250, or 30×250 mm). Gradient elution was performed with methanol/water mixtures in the presence of 0.1% TFA.

Analytical HPLC Methods Employed in Characterization of Examples

Analytical HPLC was performed on Shimadzu LC10AS liquid chromatographs using the following method:

Linear gradient of 0 to 100% solvent B over 4 min, with 1 min hold at 100% B;

UV visualization at 220 nm

Column: YMC S5 ODS Ballistic 4.6×50 mm

Flowrate: 4 ml/min

Solvent A: 0.1% trifluoroacetic acid, 90% water, 10% methanol

Solvent B: 0.1% trifluoroacetic acid, 90% methanol, 10% water

Scheme I

A solution of the chosen aromatic sulfonyl chloride (1.0 eq) in dichloromethane was added to a solution of the chosen aromatic amine (2.0 eq) in dichloromethane and stirred for 6 hours at room temperature. The resulting reaction mixture was purified by the cation exchange chromatography method described above.

Scheme II

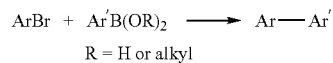

R = H or alkyl

A solution of 1.0 eq of an arylboronic acid (or ester) and the appropriate aryl bromide (1.0 eq) in 2:1 toluene:ethanol (0.1 M concentration for each reagent) was sparged with nitrogen for 15 minutes. Tetrakis (triphenylphosphine)palladium (0) (0.05 eq) and 2 M aqueous sodium carbonate (3 eq) were added and the mixture was heated at 85° C. for 3 h under a nitrogen atmosphere. The mixture was cooled and ethyl acetate and water were added. The organic layer was washed once with saturated aqueous sodium carbonate, dried over sodium sulfate, and concentrated. The residue was chromatographed on silica gel using hexanes/ethyl acetate as eluant to yield the biaryl product.

Utilities and Combinations

The compounds of formula I and salts thereof are inhibitors of 15-LO and are useful in treatment of various inflammatory disorders, including disorders involving the origin and recruitment of foam cells. The compounds of the present invention may be employed alone or in combination with each other and/or other suitable therapeutic agents useful in the treatment of 15-LO mediated disorders such as atherosclerosis, treating or preventing inflammation; diabetes; vascular restenosis; hypertension; asthma; rheumatoid arthritis; osteoarthritis; cancer; and inflammatory bowel disease.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequences of medication (such as oral contraceptives, hormome replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastesis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously).

In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with inflammatory conditions. For example, the compounds may be used to treat muscle cell damage and necrosis.

Additionally, the inventive compounds may be useful as anti-cancer and/or anti-tumor agents.

The present invention thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

The present invention also provides pharmaceutical compositions comprising at least one of the compounds of the formula I capable of treating a 15-LO mediated disorder in an amount effective therefor, and a pharmaceutically acceptable vehicle, carrier or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may also be employed in combination with other suitable therapeutic agents that a patient suffering from a 15-LO mediated disorder might also likely be taking other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

anti-arrhythmic agents including Class I agents (such as propafenone); Class II agents (such as carvedilol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in U.S. application Ser. No. 09/729,731, filed Dec. 5, 2000;

alpha- or beta-adrenergic blockers (such as propranolol, nadolol and carvedilol), or -β-adrenergic agonists such as albuterol, terbutaline, formoterol, salmeterol, bitolterol, pilbuterol, and/or fenoterol;

angiotensin-II receptor antagonists (e.g., irbesartan, losartan or valsartan);

anticholinergics such as ipratropium bromide;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-depressant or anti-anxiety agents such as nefazodone, sertraline, diazepam, lorazepam, buspirone, and hydroxyzine pamoate;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors;

anti-inflammatory agents such as cromolyn, nedocromil, theophylline, zileuton, zafirlukast, monteleukast and/or pranleukast or cortiocosteroids including beclomethasone, triamcinolone, budesonide, fluticasone, flunisolide or dexamethasone; prednisone; dexamethasone; enbrel; protein tyrosine kinase (PTK) inhibitors; cyclooxygenase inhibitors (including NSAIDs, and COX-1 and/or COX-2 inhibitors); aspirin; or indomethacin; other lipoxygenase inhibitors; chemokine receptor modulators (including CCR1, CCR2, CCR3, CXCR2 receptor antagonists); secretory and cytosolic phospholipase A2 inhibitors; VLA4 antagonists; cytokine modulators (e.g. TNF-alpha converting enzyme (TACE) inhibitors, Interleukin-1 converting enzyme (ICE) inhibitors, Interleukin-1 receptor antagonists);

angiogenesis modulators such as endostatin;

anti-oxidant agents and/or lipid peroxidation inhibitors such as probucol, BO-653, Vitamin A, Vitamin E, AGI-1067;

anti-platelet agents such as GPIIb/GPIIIa blockers, (e.g., abciximab, eptifibatide, tirofiban); P2Y$_{12}$ antagonists (e.g., clopidogrel, ticlopidine, CS-747); or thromboxane receptor antagonists (e.g., ifetroban);

anti-osteoporosis agents including alendronate and raloxifene;

anti-obesity agents including orlistat and aP2 inhibitors (such as those disclosed in U.S. Ser. No. 09/519,079 filed Mar. 6, 2000);

anti-proliferative agents for use in combination with the compounds of the present invention include cyclosporin A, paclitaxel, FK 506, and adriamycin;

anti-ulcer and gastroesophageal reflux disease agents including famotidine, ranitidine, and omeprazole;

sodium hydrogen exchanger-1 (NHE-1) inhibitors such as cariporide;

calcium channel blocking agents such as verapamil, nifedipine, diltiazem, amlodipine and mybefradil;

cardiac glycosides such as digitalis and ouabain;

diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride;

hormone replacement therapies including estrogen (e.g., congugated estrogens) and estradiol;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT1/2 inhibitors; MTP inhibitors; cholesterol absorption inhibitors such as Eztemibe; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;

mineralocorticoid receptor antagonists such as spironolactone and eplirinone;

microsomal triglyceride transport protein inhibitors (such as disclosed in U.S. Pat. Nos. 5,739,135, 5,712,279 and 5,760,246);

phosphodiesterase (PDE) inhibitors including dipyridamole, cilostazol, or sildenafil, or PDE inhibitors in combination with aspirin, ifetroban, picotamide, ketanserin, clopidogrel, and/or thromboxane receptor antagonists or thromboxane A synthetase inhibitors (such as picotamide);

serotonin-2-receptor antagonists (such as ketanserin), fibrinogen receptor antagonists; and thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), factor VIIa inhibitors, factor Xa inhibitors, thrombin inhibitors (such as hirudin and argatroban), animal salivary gland plasminogen activators, PAI-1 inhibitors such as XR-330 and T-686, and inhibitors of α-2-antiplasmin such as anti-α-2-antiplasmin antibody, prostacyclin mimetics.

The inventive compounds may also be useful in combination with other anticancer strategies and chemotherapies such as taxol and/or cisplatin. The compounds may be used in conjunction with anti-tumor agents such as paclitaxel, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to allow for increased efficacy and/or reduced doses of any of the above agents and therefore minimize potential hemorrhagic side-effects.

If formulated as a fixed dose, such combination products employ the compounds of this invention within the dosage range described and the other pharmaceutically active agent within its effective dosage range. The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound as a 15-LO inhibitor. Compounds described in the following Examples have demonstrated measurable activity as 15-LO inhibitors. The inhibitory activity of the Examples against purified 15-LO enzyme was determined using a standard colorimetric assay in which the lipid hydroperoxide product of either linoleic or arachidonic acid [13-hydroperoxyoctadecadienoic acid (13-HPODE) and 15-hydroperoxyeicosatetraenoic acid (15-HPETE), respectively] oxidizes Fe2+ under mildly acidic conditions [Jiang et al, Lipids (1991), 26:10, 853-856]. The Fe3+ forms a chromophore with xylenol orange that absorbs strongly at 560 nm. Inhibitory activity was compared to an uninhibited (maximal) reaction to yield % inhibition (compound concentration in which enzyme activity is reduced by 50% is termed the $IC_{50}$). 15-LO enzyme was obtained from phenylhydrazine-treated rabbits and purified according to the method of Rapoport et al [European Journal of Biochemistry (1979) 96:545-561]. In addition to the calorimetric assay, a standard spectrophotometric kinetic assay [Gan et al, *J. Biological Chemistry* (1996), 271:41; 25412-2541877] was also employed to measure compound activity as 15-LO inhibitors. This assay determines enzyme activity by monitoring the increased absorbance at 234 nm that results from conjugated diene formation of the metabolized substrate. Reactions were carried out 3 minutes and the linear part of the curve was utilized to calculate reaction rates. IC50 calculations were as described for the colorimetric assay.

EXAMPLES

The following Examples illustrate embodiments of the present invention, and are not intended to limit the scope of the claims.

Example 1

N-[2-(1H-Indol-3-yl)-ethyl]4-pentyl-benzene-sulfonamide

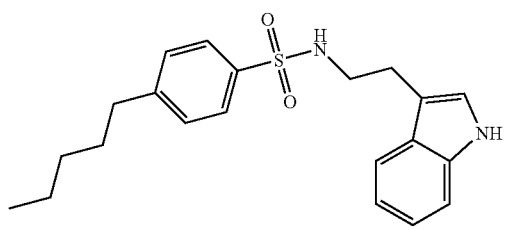

To a solution of tryptamine (19.2 mg, 0.12 mmol) in 2 ml $CH_2Cl_2$ was added 0.06 mmol of 4-n-butylphenylsulfonyl chloride in $CH_2Cl_2$, followed by 16.5 μl of triethylamine. After stirring the reaction for 6 hr at room temperature, the mixture was purified by loading on to a cation exchange resin and the resin was eluted using $CH_2Cl_2$. The appropriate fractions were combined and evaporated to give the product. $^1H$ NMR ($CDCl_3$): δ 0.89 (t, 3H), 1.3 (m, 4H), 1.6 (m, 2H), 2.65 (t, 2H), 2.96 (t, 2H), 3.3 (m, 2H), 6.9-7.4 (m, 6H), 7.6 (d, 2H), 8.0 (s, 1H).

MS m/e 371; HPLC retention time 4.38 min

Examples 2 to 71

The following compounds 2 to 71 were prepared by a solution phase combinatorial chemistry method similar to the one described for Example 1 using tryptamine and the corresponding arylsulfonyl chloride in the presence of triethylamine. The products were purified by catin ion-exchange chromatography according to the General Method. HLPC retention times were determined using HPLC Method described in the General Method.

| Ex.# | Structure | Name | M + H | Rt(min) |
| --- | --- | --- | --- | --- |
| 2 | 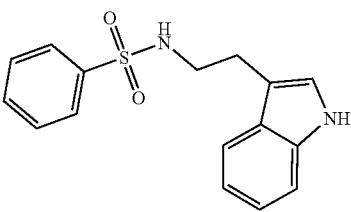 | N-[2-(1H-Indol-3-yl)ethyl]-benzenesulfonamide | 301 | 1.48 |
| 3 | 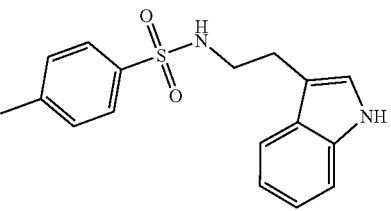 | N-[2-(1H-Indol-3-yl)-ethyl]-4-methyl-benzenesulfonamide | 315 | 1.59 |
| 4 | 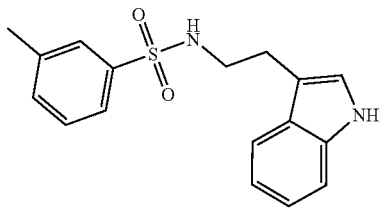 | N-[2-(1H-Indol-3-yl)-ethyl]-3-methyl-benzenesulfonamide | 315 | 1.59 |
| 5 | 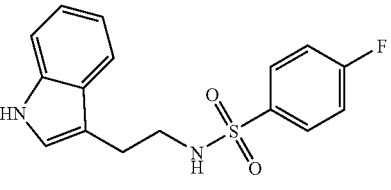 | N-[2-(1H-Indol-3-yl)-ethyl]-4-fluoro-benzenesulfonamide | 319 | 1.52 |
| 6 | 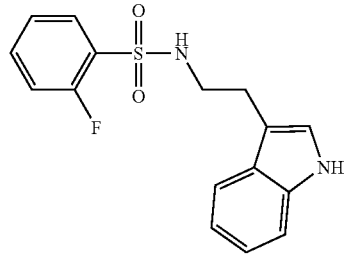 | N-[2-(1H-Indol-3-yl)-ethyl]-2-fluoro-benzenesulfonamide | 319 | 1.4 |
| 7 | 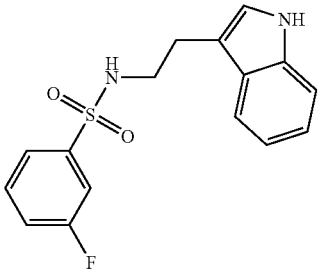 | N-[2-(1H-Indol-3-yl)-ethyl]-3-fluoro-benzenesulfonamide | 319 | 1.55 |

-continued

| Ex.# | Structure | Name | M + H | Rt(min) |
|---|---|---|---|---|
| 8 | 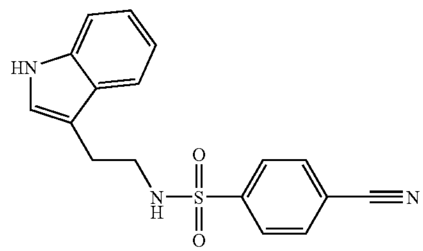 | N-[2-(1H-Indol-3-yl)-ethyl]-4-cyano-benzenesulfonamide | 326 | 1.44 |
| 9 | 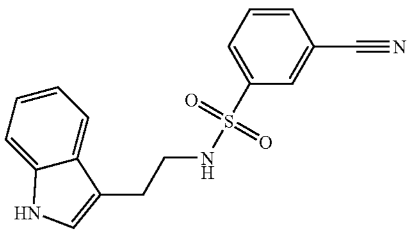 | N-[2-(1H-Indol-3-yl)-ethyl]-3-cyano-benzenesulfonamide | 326 | 1.41 |
| 10 | 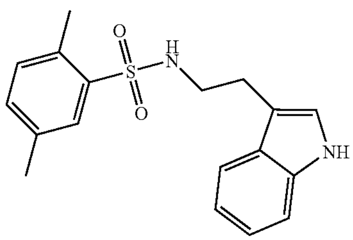 | N-[2-(1H-Indol-3-yl)-ethyl]-2,5-dimethyl-benzenesulfonamide | 329 | 1.69 |
| 11 | 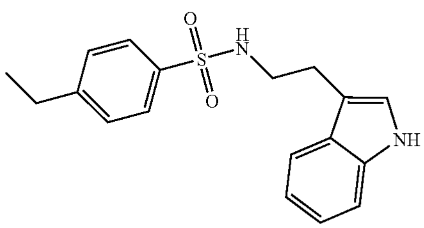 | N-[2-(1H-Indol-3-yl)-ethyl]-4-ethyl-benzenesulfonamide | 329 | 1.7 |
| 12 | 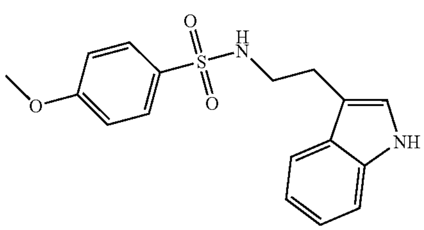 | N-[2-(1H-Indol-3-yl)-ethyl]-4-methoxy-benzenesulfonamide | 331 | 1.51 |
| 13 | 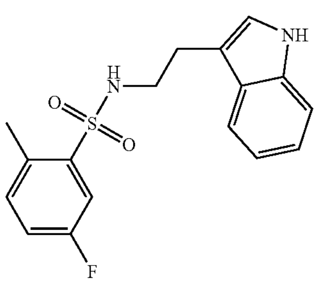 | N-[2-(1H-Indol-3-yl)-ethyl]-2-methyl-5-fluoro-benzenesulfonamide | 333 | 1.64 |

-continued

| Ex.# | Structure | Name | M + H | Rt(min) |
| --- | --- | --- | --- | --- |
| 14 | 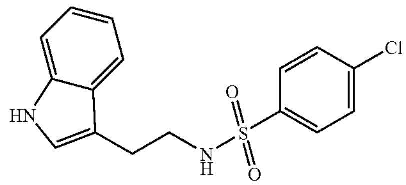 | N-[2-(1H-Indol-3-yl)-ethyl]-4-chloro-benzenesulfonamide | 335 | 1.66 |
| 15 | 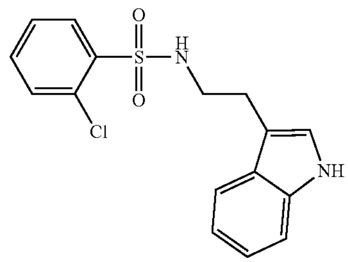 | N-[2-(1H-Indol-3-yl)-ethyl]-2-chloro-benzenesulfonamide | 335 | 1.5 |
| 16 | 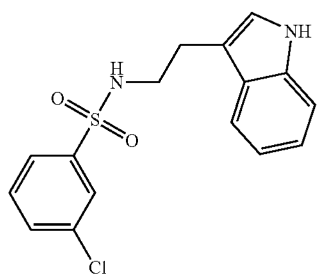 | N-[2-(1H-Indol-3-yl)-ethyl]-3-chloro-benzenesulfonamide | 335 | 1.65 |
| 17 | 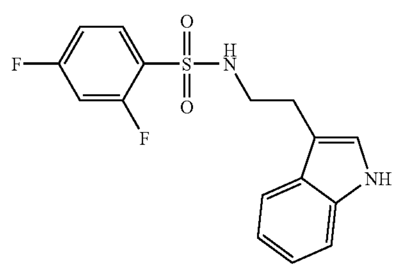 | N-[2-(1H-Indol-3-yl)-ethyl]-2,4-difluoro-benzenesulfonamide | 337 | 1.54 |
| 18 | 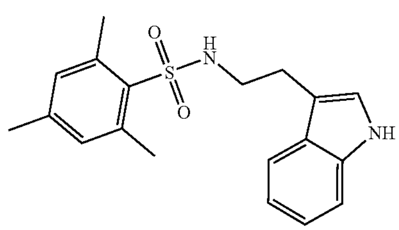 | N-[2-(1H-Indol-3-yl)-ethyl]-2,4,6-trimethyl-benzenesulfonamide | 343 | 1.8 |
| 19 | 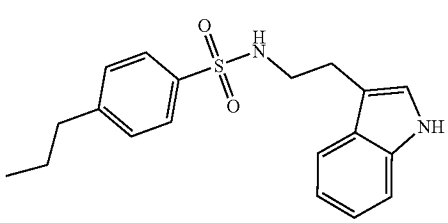 | N-[2-(1H-Indol-3-yl)-ethyl]-4-propyl-benzenesulfonamide | 343 | 1.81 |

-continued

| Ex.# | Structure | Name | M + H | Rt(min) |
|---|---|---|---|---|
| 20 | 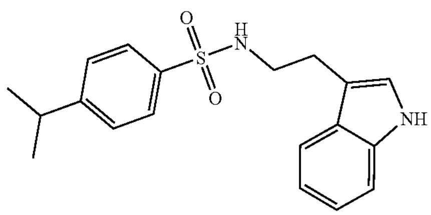 | N-[2-(1H-Indol-3-yl)-ethyl]-4-isopropyl-benzenesulfonamide | 343 | 1.78 |
| 21 | 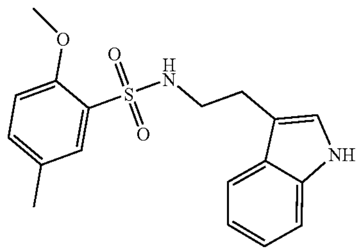 | N-[2-(1H-Indol-3-yl)-ethyl]-2-methoxy-5-methyl-benzenesulfonamide | 345 | 1.55 |
| 22 | 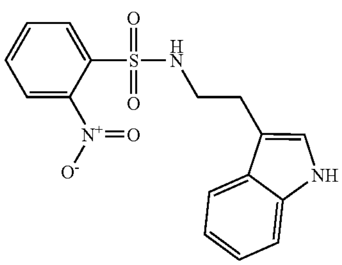 | N-[2-(1H-Indol-3-yl)-ethyl]-2-nitro-benzenesulfonamide | 345 | 2.7 |
| 23 | 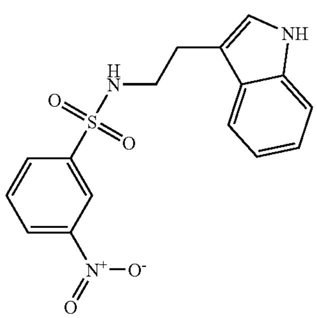 | N-[2-(1H-Indol-3-yl)-ethyl]-3-nitro-benzenesulfonamide | 346 | 1.5 |
| 24 | 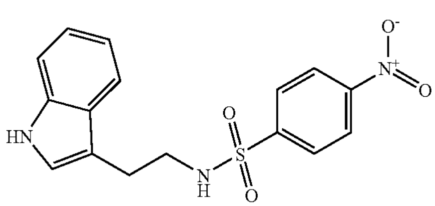 | N-[2-(1H-Indol-3-yl)-ethyl]-4-nitro-benzenesulfonamide | 346 | 1.54 |
| 25 | 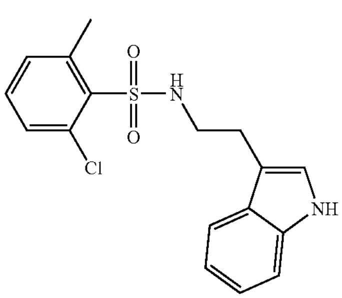 | N-[2-(1H-Indol-3-yl)-ethyl]-2-chloro-6-methyl-benzenesulfonamide | 349 | 1.64 |

-continued

| Ex.# | Structure | Name | M + H | Rt(min) |
|---|---|---|---|---|
| 26 | 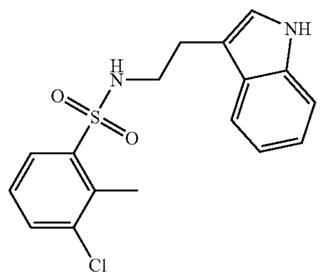 | N-[2-(1H-Indol-3-yl)-ethyl]-2-methyl-3-chlorol-benzenesulfonamide | 349 | 1.74 |
| 27 | 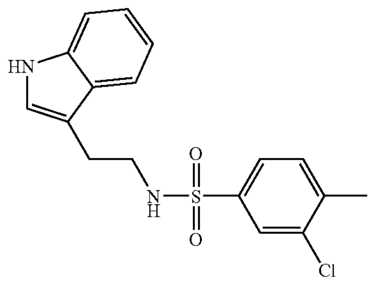 | N-[2-(1H-Indol-3-yl)-ethyl]-3-chloro-4-methyl-benzenesulfonamide | 349 | 1.74 |
| 28 | 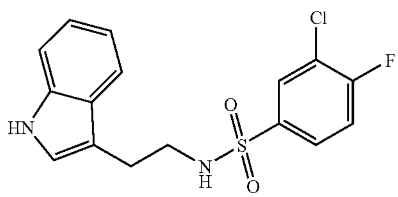 | N-[2-(1H-Indol-3-yl)-ethyl]-3-chloro-4-fluoro-benzenesulfonamide | 352 | 1.62 |
| 29 | 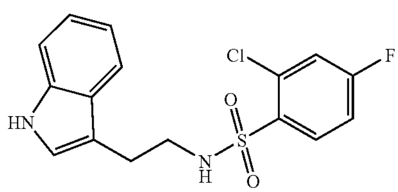 | N-[2-(1H-Indol-3-yl)-ethyl]-2-chloro-4-fluoro-benzenesulfonamide | 353 | 1.61 |
| 30 | 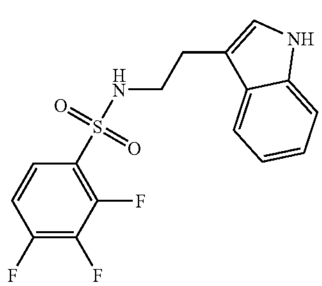 | N-[2-(1H-Indol-3-yl)-ethyl]-2,3,4-trifluoro-benzenesulfonamide | 355 | 1.57 |
| 31 | 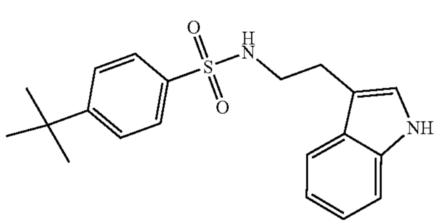 | N-[2-(1H-Indol-3-yl)-ethyl]-4-tert-butyl-benzenesulfonamide | 357 | 1.85 |

-continued

| Ex.# | Structure | Name | M + H | Rt(min) |
|---|---|---|---|---|
| 32 | 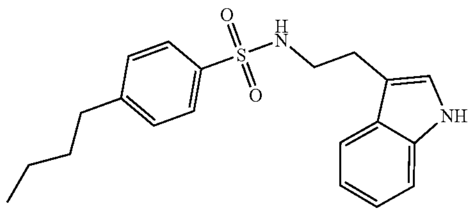 | N-[2-(1H-Indol-3-yl)-ethyl]-4-butyl-benzenesulfonamide | 357 | 1.91 |
| 33 | 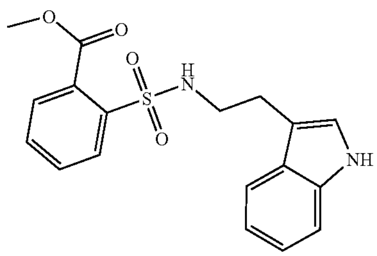 | 2-[2-(1H-Indol-3-yl)-ethylsulfamoyl]-benzoic acid methyl ester | 359 | 1.52 |
| 34 | 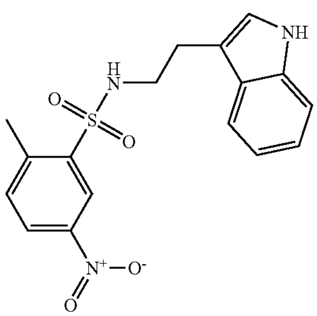 | N-[2-(1H-Indol-3-yl)-ethyl]-2-methyl-5-nitro-benzenesulfonamide | 359 | 1.53 |
| 35 | 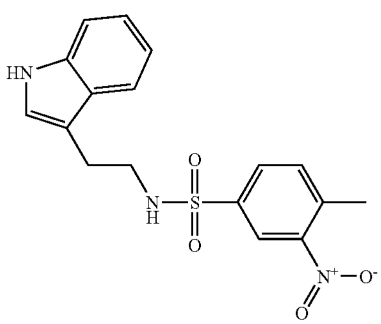 | N-[2-(1H-Indol-3-yl)-ethyl]-4-methyl-3-nitro-benzenesulfonamide | 359 | 1.57 |
| 36 | 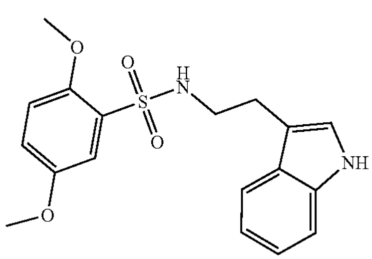 | N-[2-(1H-Indol-3-yl)-ethyl]-2,5-dimethoxy-benzenesulfonamide | 361 | 1.55 |

| Ex.# | Structure | Name | M + H | Rt(min) |
|---|---|---|---|---|
| 37 | 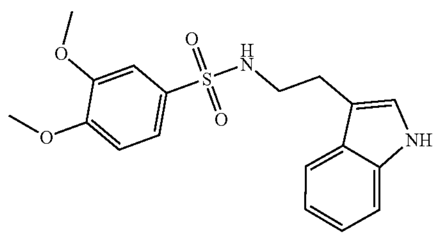 | N-[2-(1H-Indol-3-yl)-ethyl]-3,4-dimethoxy-benzenesulfonamide | 361 | 1.39 |
| 38 | 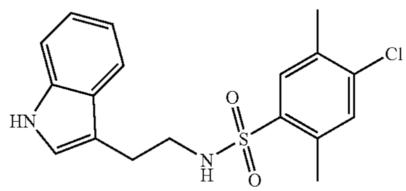 | 4-Chloro-N-[2-(1H-indol-3-yl)-ethyl]-2,5-dimethyl-benzenesulfonamide | 363 | 1.86 |
| 39 | 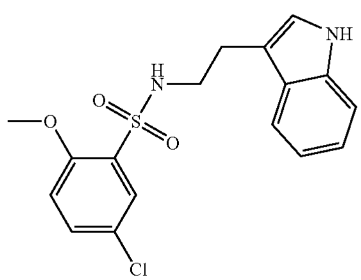 | N-[2-(1H-Indol-3-yl)-ethyl]-3-chloro-6-methoxy-benzenesulfonamide | 365 | 1.63 |
| 40 | 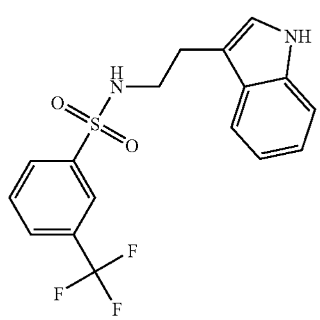 | N-[2-(1H-Indol-3-yl)-ethyl]-3-trifluoromethyl-benzenesulfonamide | 369 | 1.71 |
| 41 | 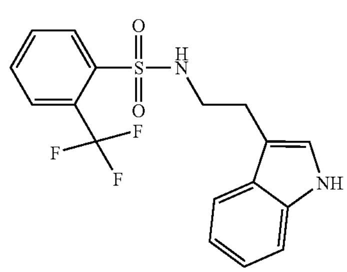 | N-[2-(1H-Indol-3-yl)-ethyl]-2-trifluoromethyl-benzenesulfonamide | 369 | 1.56 |
| 42 | 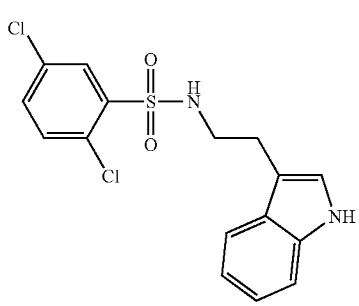 | N-[2-(1H-Indol-3-yl)-ethyl]-2,5-dichloro-benzenesulfonamide | 369 | 1.72 |

-continued

| Ex.# | Structure | Name | M + H | Rt(min) |
|---|---|---|---|---|
| 43 | 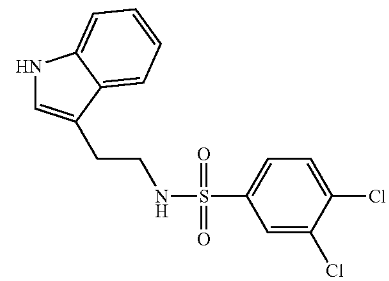 | N-[2-(1H-Indol-3-yl)-ethyl]-3,4-dichloro-benzenesulfonamide | 369 | 1.8 |
| 44 | 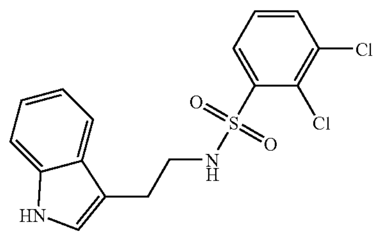 | N-[2-(1H-Indol-3-yl)-ethyl]-2,3-dichloro-benzenesulfonamide | 369 | 1.66 |
| 45 | 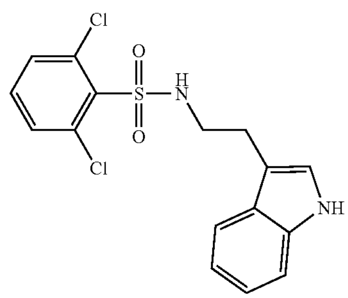 | N-[2-(1H-Indol-3-yl)-ethyl]-2,6-dichloro-benzenesulfonamide | 369 | 1.6 |
| 46 | 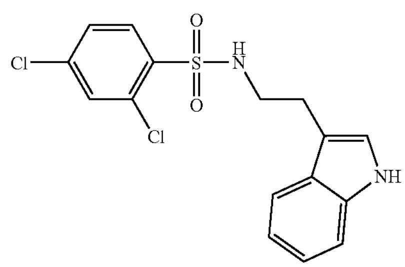 | N-[2-(1H-Indol-3-yl)-ethyl]-2,4-dichloro-benzenesulfonamide | 369 | 1.74 |
| 47 | 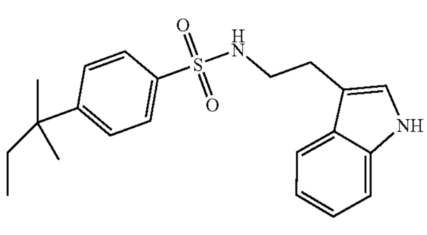 | 4-(1,1-Dimethyl-propyl)-N-[2-(1H-indol-3-yl)-ethyl]-benzenesulfonamide | 371 | 1.92 |
| 48 | 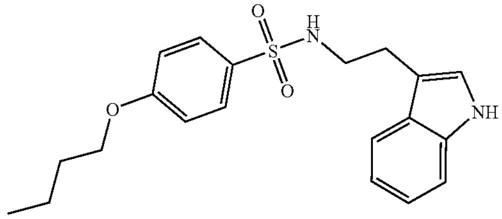 | 4-Butoxy-N-[2-(1H-indol-3-yl)-ethyl]-benzenesulfonamide | 373 | 1.85 |

-continued
| Ex.# | Structure | Name | M + H | Rt(min) |
|---|---|---|---|---|
| 49 | 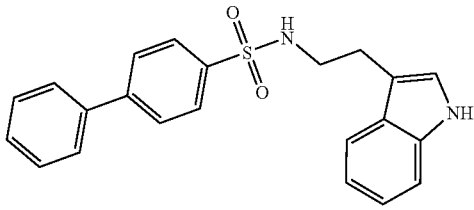 | Biphenyl-4-sulfonic acid [2-(1H-indol-3-yl)-ethyl]-amide | 377 | 1.82 |
| 50 | 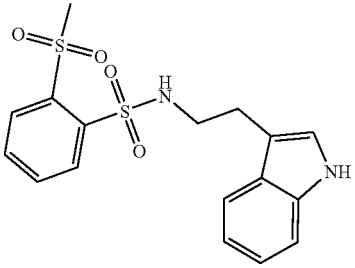 | N-[2-(1H-Indol-3-yl)-ethyl]-2-methanesulfonyl-benzenesulfonamide | 379 | 1.46 |
| 51 | 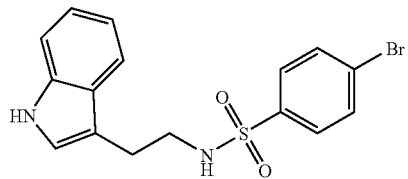 | N-[2-(1H-Indol-3-yl)-ethyl]-4-bromo-benzenesulfonamide | 379 | 1.7 |
| 52 | 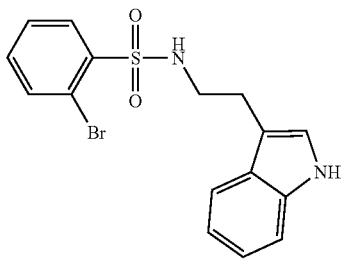 | N-[2-(1H-Indol-3-yl)-ethyl]-2-bromo-benzenesulfonamide | 379 | 1.55 |
| 53 | 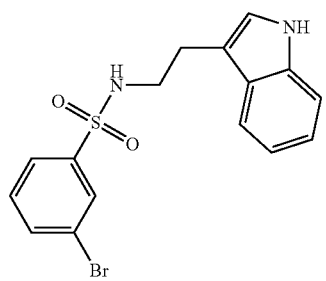 | N-[2-(1H-Indol-3-yl)-ethyl]-3-bromo-benzenesulfonamide | 379 | 1.68 |
| 54 | 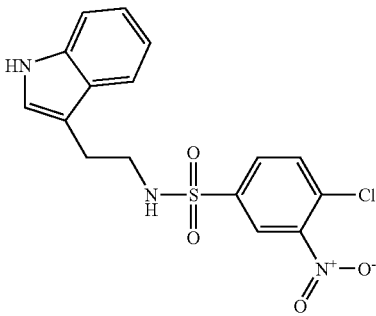 | N-[2-(1H-Indol-3-yl)-ethyl]-4-chloro-3-nitro-benzenesulfonamide | 380 | 1.64 |

| Ex.# | Structure | Name | M + H | Rt(min) |
|---|---|---|---|---|
| 55 | 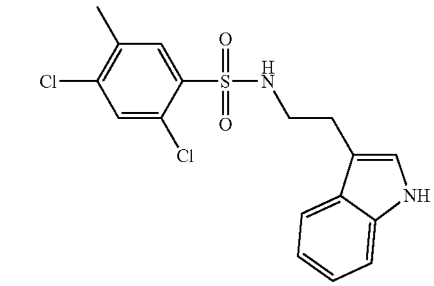 | N-[2-(1H-Indol-3-yl)-ethyl]-2,4-dichloro-5-methyl-benzenesulfonamide | 383 | 1.76 |
| 56 | 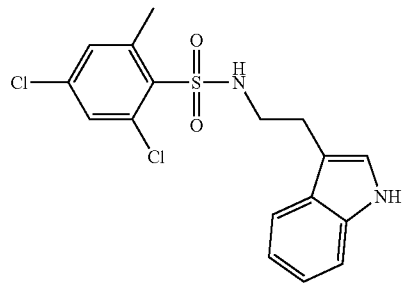 | N-[2-(1H-Indol-3-yl)-ethyl]-2,4-dichloro-6-methyl-benzenesulfonamide | 383 | 1.83 |
| 57 | 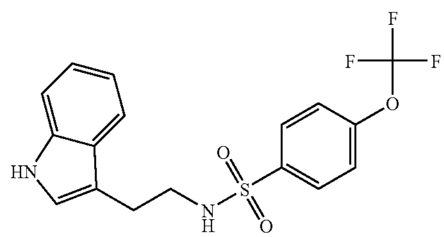 | N-[2-(1H-Indol-3-yl)-ethyl]-4-trifluoromethoxy-benzenesulfonamide | 385 | 1.76 |
| 58 | 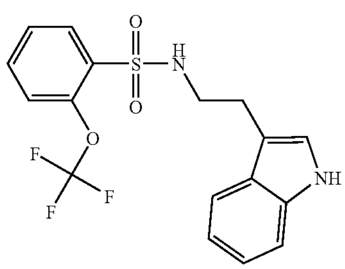 | N-[2-(1H-Indol-3-yl)-ethyl]-2-trifluoromethoxy-benzenesulfonamide | 385 | 1.6 |
| 59 | 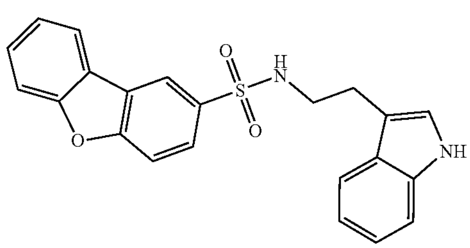 | Dibenzofuran-2-sulfonic acid [2-(1H-indol-3-yl)-ethyl]-amide | 391 | 1.84 |

-continued

| Ex.# | Structure | Name | M + H | Rt(min) |
|---|---|---|---|---|
| 60 | 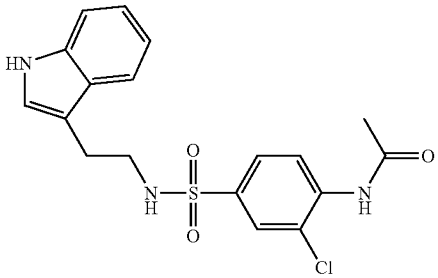 | N-{2-Chloro-4-[2-(1H-indol-3-yl)-ethylsulfamoyl]-phenyl}-acetamide | 392 | 2.76 |
| 61 | 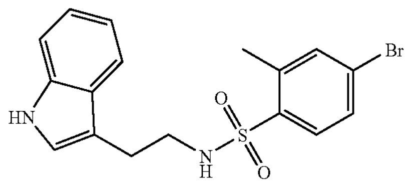 | 4-Bromo-N-[2-(1H-indol-3-yl)-ethyl]-2-methyl-benzenesulfonamide | 393 | 1.79 |
| 62 | 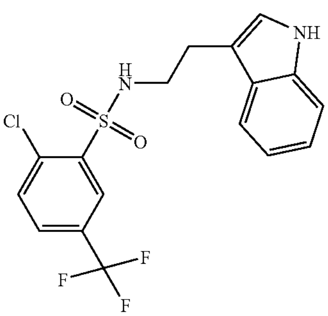 | 2-Chloro-N-[2-(1H-indol-3-yl)-ethyl]-5-trifluoromethyl-benzenesulfonamide | 403 | 1.75 |
| 63 | 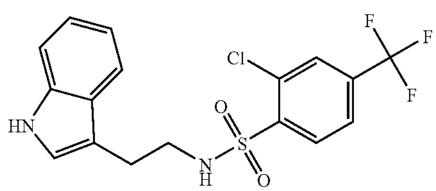 | 2-Chloro-N-[2-(1H-indol-3-yl)-ethyl]-4-trifluoromethyl-benzenesulfonamide | 403 | 1.79 |
| 64 | 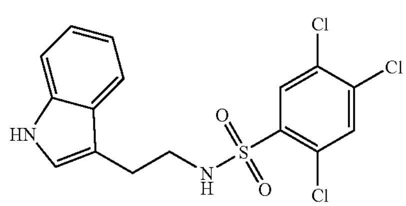 | 2,4,5-Trichloro-N-[2-(1H-indol-3-yl)-ethyl]-benzenesulfonamide | 403 | 1.87 |
| 65 | 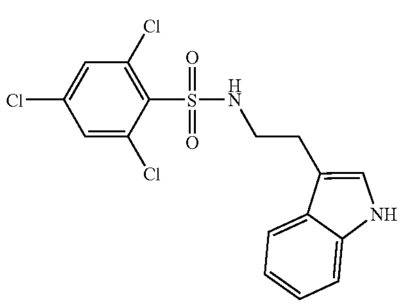 | 2,4,6-Trichloro-N-[2-(1H-indol-3-yl)-ethyl]-benzenesulfonamide | 403 | 1.81 |

-continued

| Ex.# | Structure | Name | M + H | Rt(min) |
|------|-----------|------|-------|---------|
| 66 | 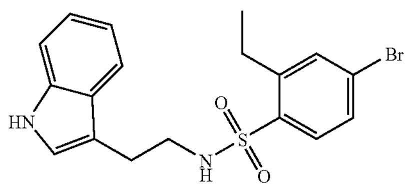 | 4-Bromo-2-ethyl-N-[2-(1H-indol-3-yl)-ethyl]-benzenesulfonamide | 407 | 1.87 |
| 67 | 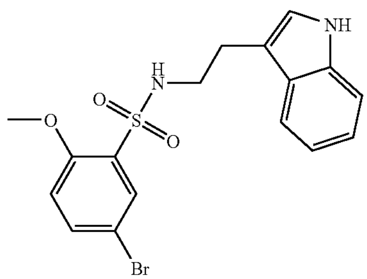 | 5-Bromo-N-[2-(1H-indol-3-yl)-ethyl]-2-methoxy-benzenesulfonamide | 409 | 1.74 |
| 68 | 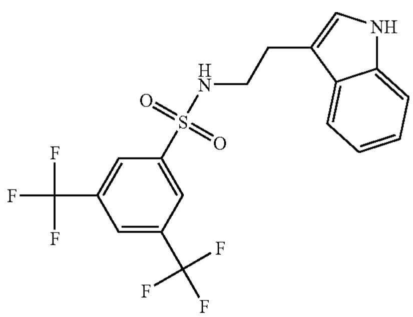 | N-[2-(1H-Indol-3-yl)-ethyl]-3,5-bis-trifluoromethyl-benzenesulfonamide | 437 | 1.81 |
| 69 | 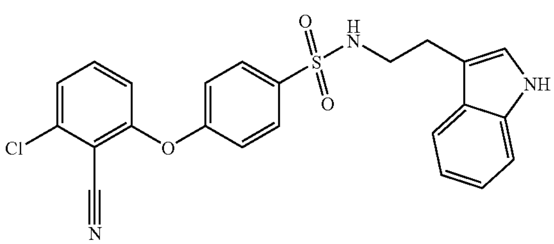 | 4-(3-Chloro-2-cyano-phenoxy)-N-[2-(1H-indol-3-yl)-ethyl]-benzenesulfonamide | 452 | 1.78 |
| 70 | 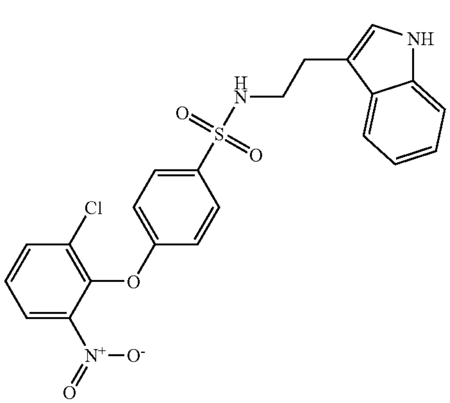 | 4-(2-Chloro-6-nitro-phenoxy)-N-[2-(1H-indol-3-yl)-ethyl]-benzenesulfonamide | 471 | 1.77 |

| Ex.# | Structure | Name | M + H | Rt(min) |
|---|---|---|---|---|
| 71 | 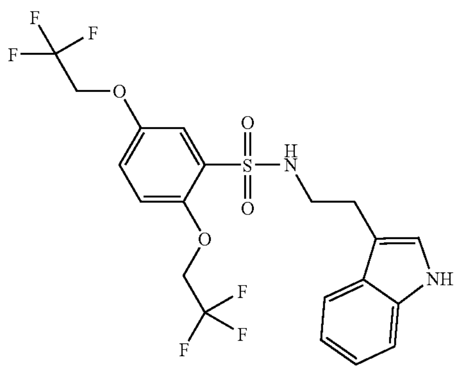 | N-[2-(1H-indol-3-yl)-ethyl]-2,5-bis-(2,2,2-trifluoro-ethoxy)-benzenesulfonamide | 497 | 1.75 |

Example 72

N-[3-(1H-Indol-3-yl)-propyl]-4-pentyl-benzene-sulfonamide

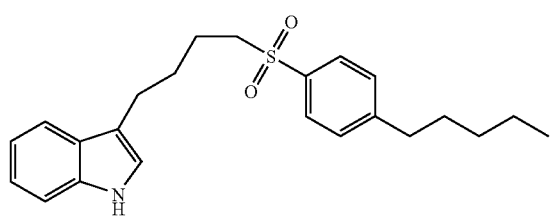

3-(1H-Indol-3-yl)-propylamine was reacted with 4-n-butylphenylsulfonyl chloride according to the procedure of Example 1. The crude residue was chromatographed on silica gel using hexanes/ethyl acetate to give 72 as a white solid. MS m/e 385; HPLC retention time 3.83 min

Example 73

N-[3-(1H-Indol-3-yl)-butyl]4-pentyl-benzene-sulfonamide

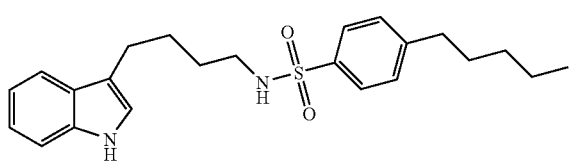

3-(1H-Indol-3-yl)-butylamine was reacted with 4-n-butylphenylsulfonyl chloride according to the procedure of Example 1. The crude residue was chromatographed on silica gel using hexanes/ethyl acetate to give 73 as a white solid. MS m/e 399; HPLC retention time 3.94 min

Example 74

4'-Methyl-biphenyl-4-sulfonic acid [2-(1H-indol-3-yl)-ethyl]-amide

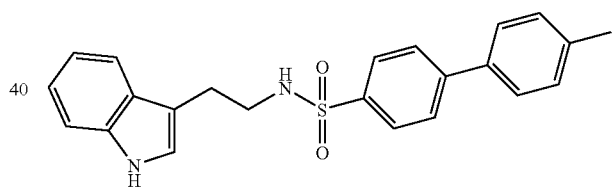

51 (75 mg, 0.19 mmol) was subjected to Suzuki coupling with 4-methyl phenylboronic acid according to General Method 1. 74 was obtained as a white solid. MS m/e 391; HPLC retention-time 3.55 min. $^1$H NMR (CDCl$_3$): δ 2.4 (s, 3H), 2.96 t, 2H), 7.5 (m, 9H), 7.6 (d, 2H), 7.8 (d, 2H).

Examples 75 to 107

The following compounds 75 to 107 were prepared by a Suzuki-coupling method similar to the one described for Example 74 using the corresponding aryl boronic acid in the presence of a suitable catalyst. HLPC retention times were determined using HPLC Method described in the General Method.

| Ex.# | Structure | Name | | M/z (MH)+ |
|---|---|---|---|---|
| 75 | 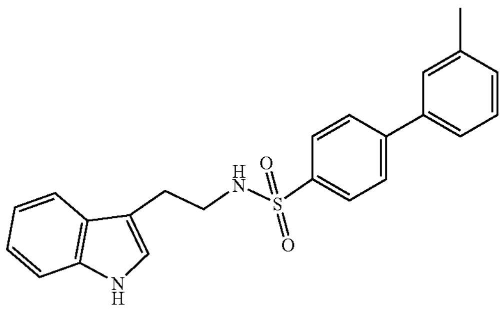 | 3'-Methyl-biphenyl-4-sulfonic acid [2-(1H-indol-3-yl)-ethyl]-amide | 3.65 | 391 |
| 76 | 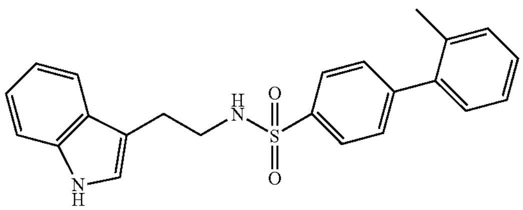 | 2'-Methyl-biphenyl-4-sulfonic acid [2-(1H-indol-3-yl)-ethyl]-amide | 3.59 | 391 |
| 77 | 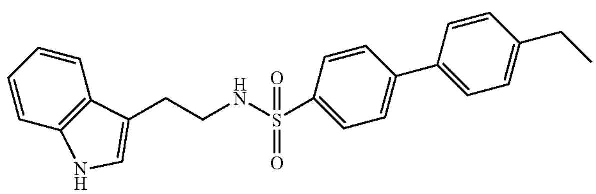 | 4'-Ethyl-biphenyl-4-sulfonic acid [2-(1H-indol-3-yl)-ethyl]-amide | 3.81 | 405 |
| 78 | 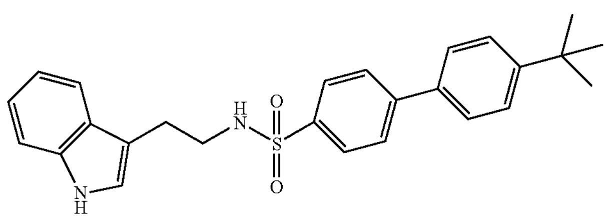 | 4'-tert-Butyl-biphenyl-4-sulfonic acid [2-(1H-indol-3-yl)-ethyl]-amide | 3.99 | 433 |
| 79 | 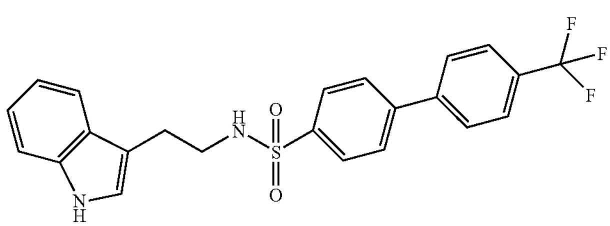 | 4'-Trifluoromethyl-biphenyl-4-sulfonic acid [2-(1H-indol-3-yl)-ethyl]-amide | 3.68 | 445 |
| 80 | 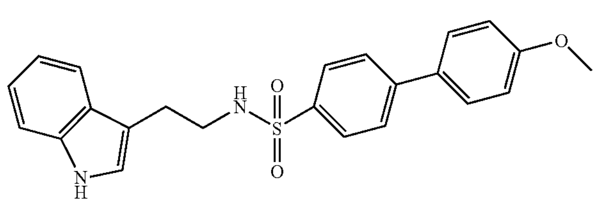 | 4'-Methoxy-biphenyl-4-sulfonic acid [2-(1H-indol-3-yl)-ethyl]-amide | 3043 | 407 |

| Ex.# | Structure | Name | | M/z (MH)+ |
|---|---|---|---|---|
| 81 | 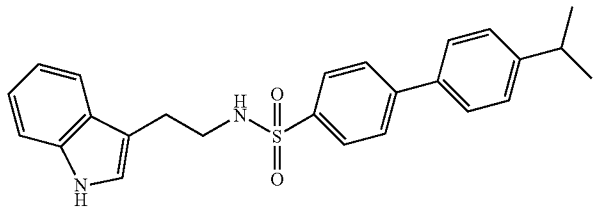 | 4'-Isopropyl-biphenyl-4-sulfonic acid [2-(1H-indol-3-yl)-ethyl]-amide | 3.92 | 419 |
| 82 | 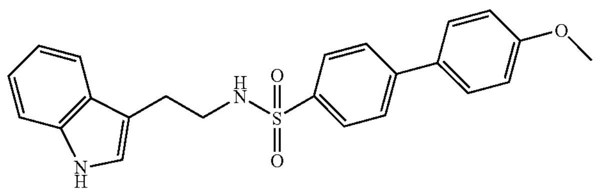 | 4'-Methylsulfanyl-biphenyl-4-sulfonic acid [2-(1H-indol-3-yl)-ethyl]-amide | 3.64 | 423 |
| 83 | 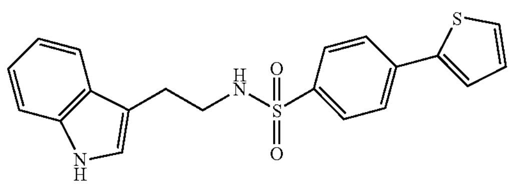 | N-[2-(1H-Indol-3-yl)-ethyl]-4-thiophen-2-yl-benzenesulfonamide | 3.2 | 383 |
| 84 | 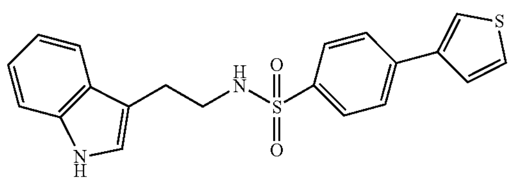 | N-[2-(1H-Indol-3-yl)-ethyl]-4-thiophen-3-yl-benzenesulfonamide | 3.31 | 383 |
| 85 | 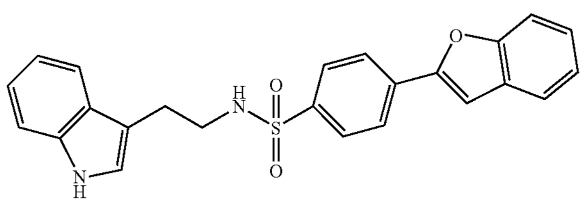 | 4-Benzofuran-2-yl-N-[2-(1H-indol-3-yl)-ethyl]-benzenesulfonamide | 3.7 | 417 |
| 86 | 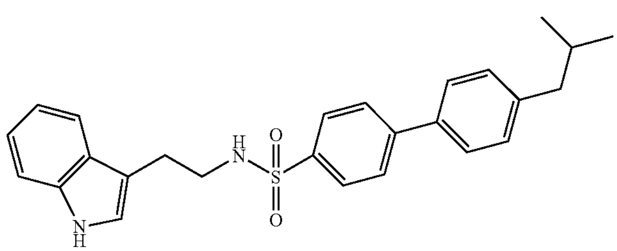 | 4'-Isobutyl-biphenyl-4-sulfonic acid [2-(1H-indol-3-yl)-ethyl]-amide | 4.06 | 433 |
| 87 | 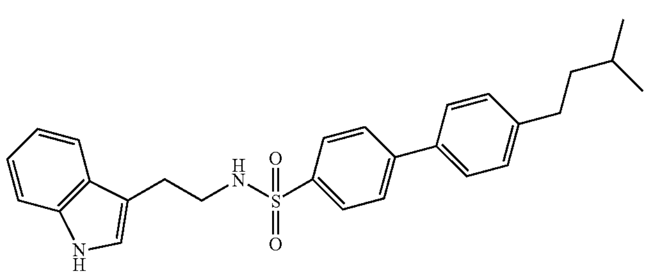 | 4'-(3-Methyl-butyl)-biphenyl-4-sulfonic acid [2-(1H-indol-3-yl)-ethyl]-amide | 4.2 | 447 |

-continued

| Ex.# | Structure | Name | | M/z (MH)+ |
|---|---|---|---|---|
| 88 | 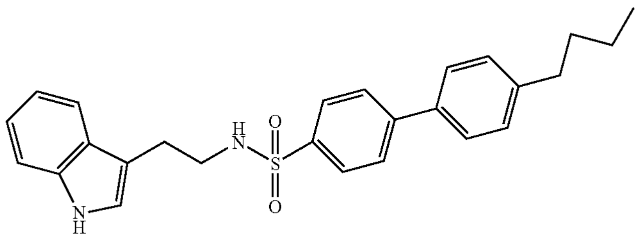 | 4'-n-Butyl-biphenyl-4-sulfonic acid [2-(1H-indol-3-yl)-ethyl]-amide | 4.1 | 433 |
| 89 | 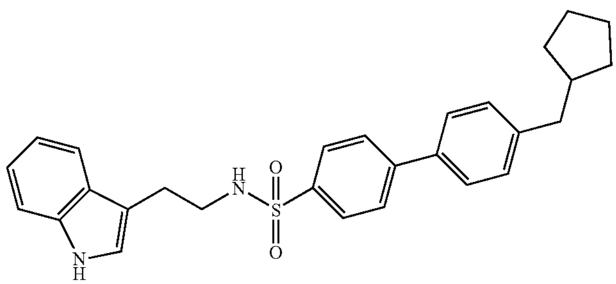 | 4'-Cyclopentylmethyl-biphenyl-4-sulfonic acid [2-(1H-indol-3-yl)-ethyl]-amide | 4.2 | 459 |
| 90 | 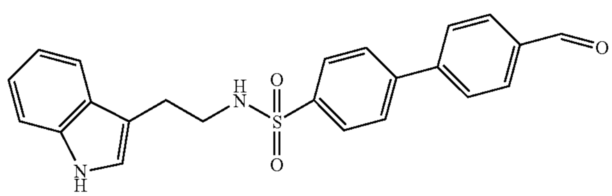 | 4'-Formylbiphenyl-4-sulfonic acid [2-(1H-indol-3-yl)-ethyl]-amide | 3.15 | 405 |
| 91 | 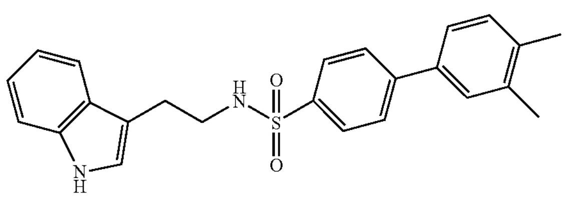 | 3',4'-Dimethyl-biphenyl-4-sulfonic acid [2-(1H-indol-3-yl)-ethyl]-amide | 3.8 | 405 |
| 92 | 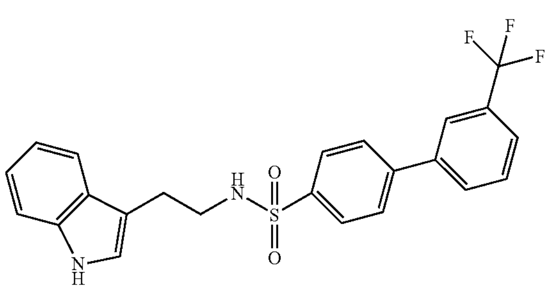 | 3'-Trifluoromethyl-biphenyl-4-sulfonic acid [2-(1H-indol-3-yl)-ethyl]-amide | 3.67 | 445 |

-continued

| Ex.# | Structure | Name | | M/z (MH)+ |
|---|---|---|---|---|
| 93 | 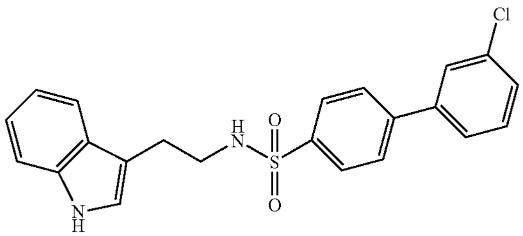 | 3'-Chloro-biphenyl-4-sulfonic acid [2-(1H-indol-3-yl)-ethyl]-amide | 3.67 | 411 |
| 94 | 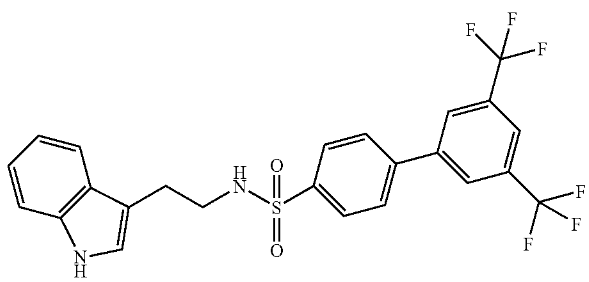 | 3',5'-Ditrifluoromethyl-biphenyl-4-sulfonic acid [2-(1H-indol-3-yl)-ethyl]-amide | 3.93 | 513 |
| 95 | 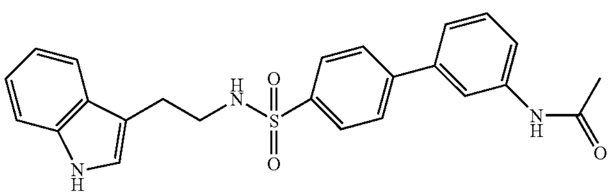 | N-{4'-[2-(1H-Indol-3-yl)-ethylsulfamoyl]-biphenyl-3-yl}-acetamide | 3.00 | 434 |
| 96 | 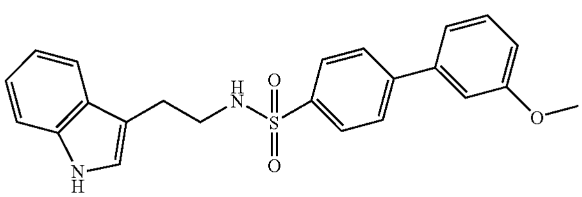 | 3'-Methoxy-biphenyl-4-sulfonic acid [2-(1H-indol-3-yl)-ethyl]-amide | 3.04 | 407 |
| 97 | 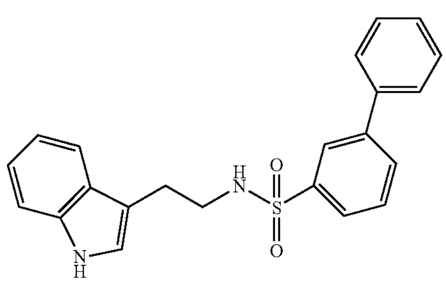 | Biphenyl-3-sulfonic acid [2-(1H-indol-3-yl)-ethyl]-amide | 3.44 | 377 |
| 98 | 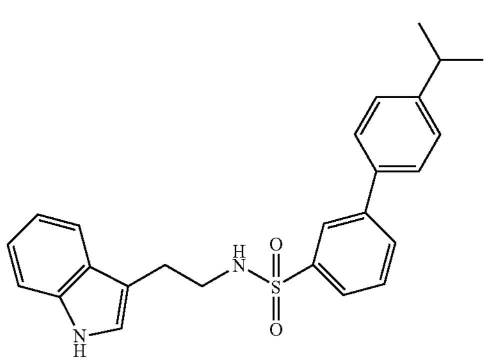 | 4'-Isopropyl-biphenyl-3-sulfonic acid [2-(1H-indol-3-yl)-ethyl]-amide | 3.86 | 419 |

-continued

| Ex.# | Structure | Name | | M/z (MH)+ |
|---|---|---|---|---|
| 99 | 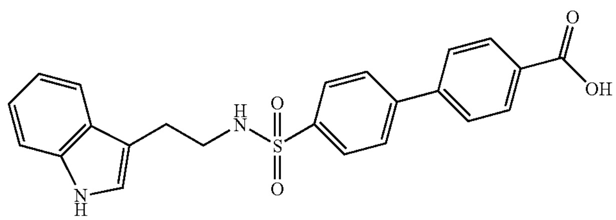 | 4'-[2-(1H-Indol-3-yl)-ethylsulfamoyl]-biphenyl-4-carboxylic acid | 3.08 | 421 |
| 100 | 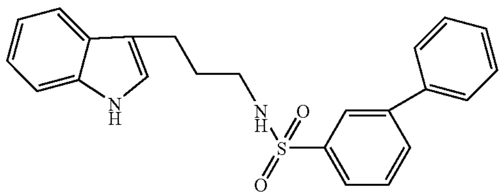 | Biphenyl-3-sulfonic acid [3-(1H-indol-3-yl)-propyl]-amide | 3.5 | 391 |
| 101 | 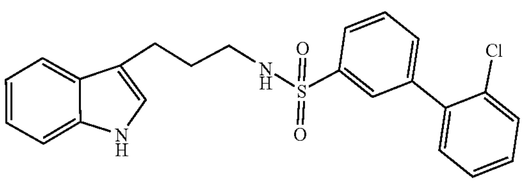 | 2'-Chloro-biphenyl-3-sulfonic acid [3-(1H-indol-3-yl)-propyl]-amide | 3.57 | 425 |
| 102 | 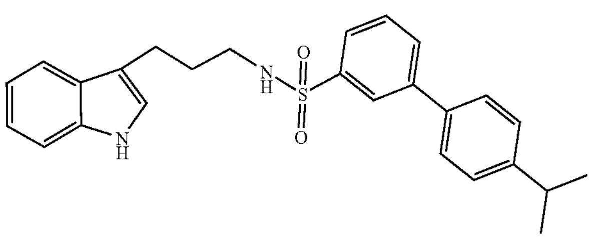 | 4'-Isopropyl-biphenyl-3-sulfonic acid [3-(1H-indol-3-yl)-propyl]-amide | 3.94 | 433 |
| 103 | 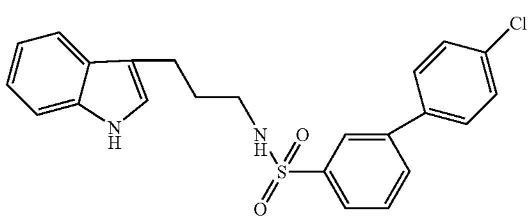 | 4'-Chloro-biphenyl-3-sulfonic acid [3-(1H-indol-3-yl)-propyl]-amide | 3.71 | 425 |
| 104 | 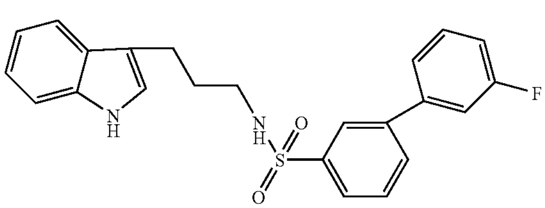 | 3'-Fluoro-biphenyl-3-sulfonic acid [3-(1H-indol-3-yl)-propyl]-amide | 3.54 | 408 |

-continued

| Ex.# | Structure | Name | | M/z (MH)+ |
|---|---|---|---|---|
| 105 | 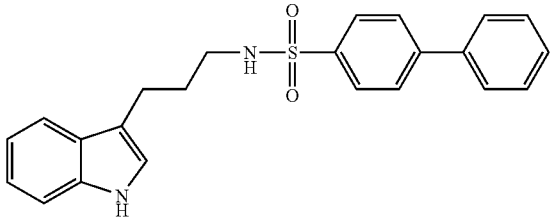 | Biphenyl-4-sulfonic acid [3-(1H-indol-3-yl)-propyl]-amide | 3.52 | 391 |
| 106 | 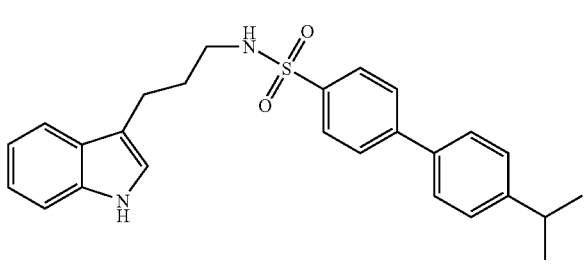 | 4'-Isopropyl-biphenyl-4-sulfonic acid [3-(1H-indol-3-yl)-propyl]-amide | 3.94 | 433 |
| 107 | 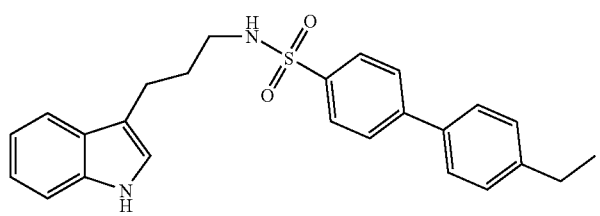 | 4'-Ethyl-biphenyl-4-sulfonic acid [3-(1H-indol-3-yl)-propyl]-amide | 3.85 | 419 |

Example 108

4-[2-(1H-Indol-3-yl)-ethylsulfamoyl]-benzoic acid

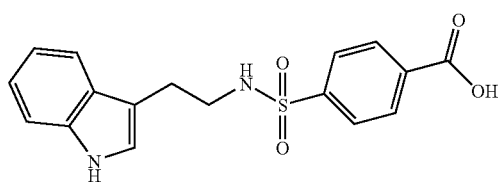

To 3.0 g (18.7 mmol) of tryptamine in 20 ml of CH$_2$Cl$_2$ was added, 2.5 ml (18.7 mmol) of triethylamine followed by 2.06 g (9.4 mmol) of 4-(chlorosulphonyl) benzoic acid. After stirring for 2 h, the mixture was extracted with CH$_2$Cl$_2$ (3×50 ml) and the combined organic extracts were washed with water and dried and evaporated. The residue was chromatographed on silica gel using 2:98:0.5 MeOH/CH$_2$Cl$_2$/AcOH to afford the title compound as a solid. MS m/e 345; HPLC retention time 2.52 min.

Example 109

4-[2-(1H-Indol-3-yl)-ethylsulfamoyl]-N-phenyl-benzamide

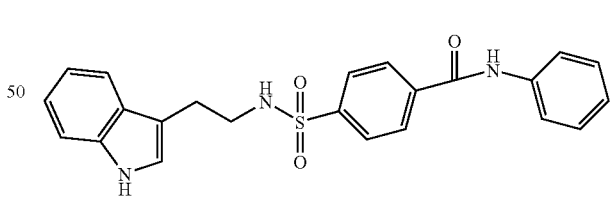

To 50 mg (0.14 mmol) of 108 in 2 ml DMF was added 17.5 mg (0.18 mmol) of aniline, and 23 mg (0.18 mmol) of DMAP, followed by 36 mg (0.18 mmol) of EDAC. The mixture was stirred at room temperature for 12 hr. The mixture was diluted with EtOAc (5 ml) and washed with 1% aqueous HCl, water and dried and evaporated. The residue was triturated with hexane to give the title compound as a white solid. MS m/e 420; HPLC retention time 2.98 min. $^1$H NMR (DMSO-D6): δ 2.8 (t, 2H), 3.03 (t, 2H), 6.95 (t, 1H), 7.04 (t, 1H), 7.13 (m, 2H), 7.30-7.4 (m, 4H), 7.7 (d, 2H), 7.9 (m, 2H), 8.0 (d, 2H).

Example 110

N-Benzyl-4-[2-(1H-indol-3-yl)-ethylsulfamoyl]-benzamide

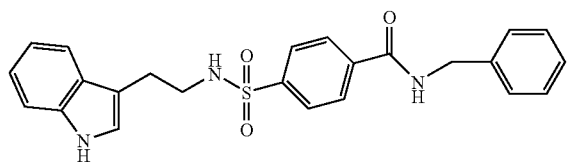

108 was reacted with benzylamine according to the procedure of Example 109 to afford the title compound as a white solid. MS m/e 434; HPLC retention time 2.95 min. $^1$H NMR (DMSO-D6): δ 2.8 (t, 2H), 3.01 (t, 2H), 4.48 (d, 2H), 6.93 (t, 1H), 7.11 (t, 1H), 7.2 (m, 2H), 7.30-7.4 (m, 6H), 7.8 (m, 3H), 8.0 (d, 2H).

Example 111

N-[2-(1H-Indol-3-yl)-ethyl]-4-phenoxymethyl-benzenesulfonamide

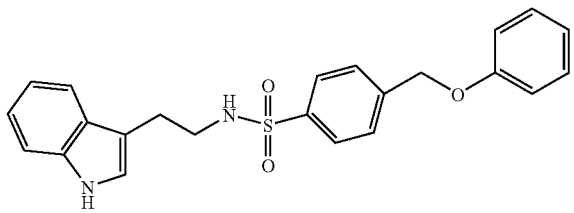

MS m/e 407; HPLC retention time 4.06 min

Example 112

3-{4-[3-(4-Pentyl-benzenesulfonylamino)-propoxy]-phenyl}-propionic acid methyl ester

A. N-(3-Bromo-propyl)-4-pentyl-benzenesulfonamide

To 4.0 g (18.3 mmol) of 3-bromopropylamine in 20 ml of CH$_2$Cl$_2$ was added, 2.5 ml (18.3 mmol) of triethylamine followed by 2 g (39 mmol) of 4-pentylbenzenesulphonylchloride. After stirring for 2 hr, the mixture was extracted with CH2Cl2 (3×50 ml) and the combined organic extracts were washed with water and dried and evaporated. The residue was triturated with hexane to give 112A.

B. 3-{4-[3-(4-Pentyl-benzenesulfonylamino)-propoxy]-phenyl}-propionic acid methyl ester To 216 mg (1.2 mmol) of phenol in 5 ml DMF was added 48 mg (1.2 mmol) of NaH. After stirring for 0.5 h, 200 mg (1.2 mmol) of 112A in DMF was added and the mixture was stirred at room temperature overnight. The mixture was diluted with EtOAc (100 ml) and washed with water and dried and evaporated. The residue was chromatographed on silica gel using 3:7 EtOAc/hexane to afford the title compound as a solid. MS m/e 448; HPLC retention time 3.89 min

Examples 113 to 119

The following compounds 113 to 119 were prepared by a method similar to the one described for Example 112 using 112A. HLPC retention times were determined using HPLC Method described in the General Method.

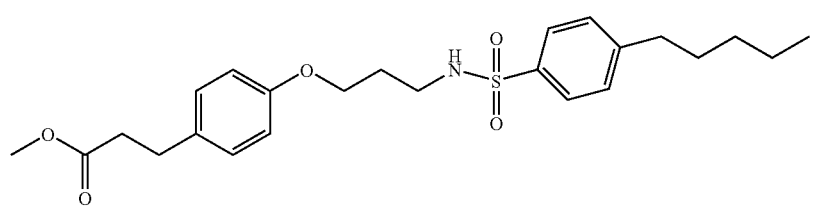

| Ex.# | Structure | Name | Rt(min) | M + H |
|---|---|---|---|---|
| 113 | 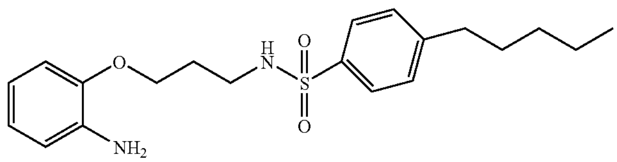 | N-[3-(2-Amino-phenoxy)-propyl]-4-pentyl-benzenesulfonamide | 2.9 | 377 |
| 114 | 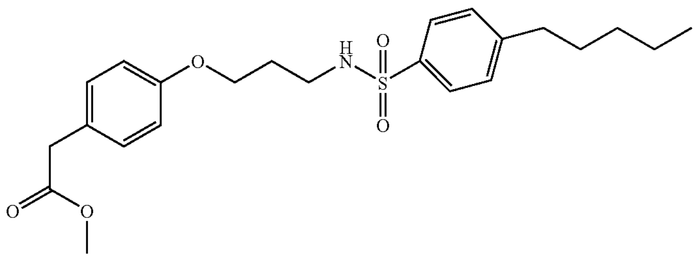 | {4-[3-(4-Pentyl-benzenesulfonyl-amino)-propoxy]-phenyl}-acetic acid methyl ester | 3.8 | 434 |
| 115 | 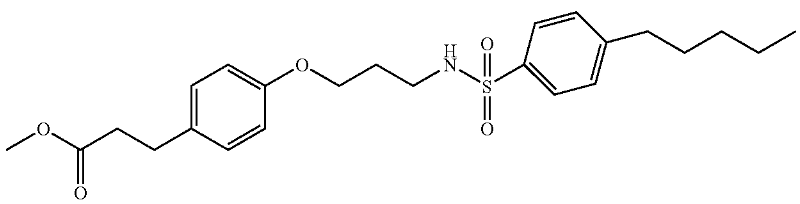 | 3-{4-[3-(4-Pentyl-benzenesulfonyl-amino)-propoxy]-phenyl}-propionic acid methyl ester | 3.8 | 448 |
| 116 | 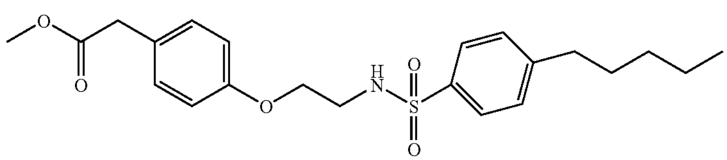 | {4-[2-(4-Pentyl-benzenesulfonyl-amino)-ethoxy]-phenyl}-acetic acid methyl ester | 3.7 | 420 |
| 117 | 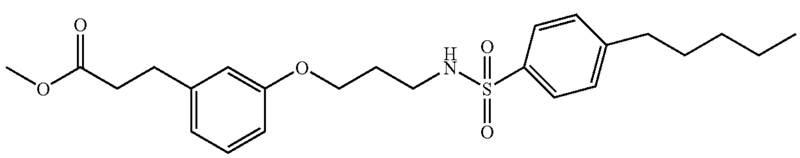 | 3-{3-[3-(4-Pentyl-benzenesulfonyl-amino)-propoxy]-phenyl}-propionic acid methyl ester | 3.9 | 448 |
| 118 | 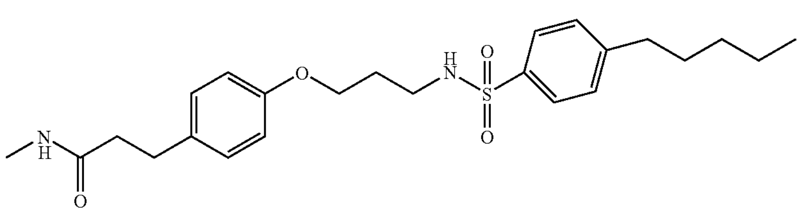 | N-Methyl-3-{4-[3-(4-pentyl-benzenesulfonyl-amino)-propoxy]-phenyl}-propionamide | 3.54 | 447 |
| 119 | 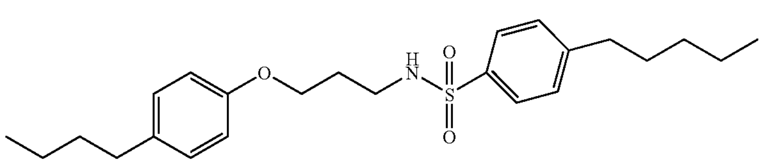 | N-[3-(4-Butyl-phenoxy)-propyl]-4-pentyl-benzenesulfonamide | 4.36 | 418 |

Example 120

3-{4-[3-(4-Pentyl-benzenesulfonylamino)-propoxy]-phenyl}-propionic acid

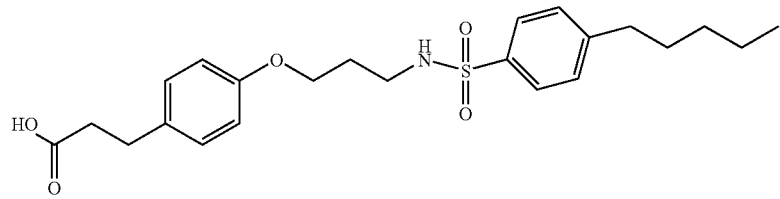

Treatment of 115 in aqueous methanol with 1N aqueos sodium hydroxide afforded the title compound. MS m/e 434; HPLC retention time 3.70 min

Example 121

{4-[3-(4-Pentyl-benzenesulfonylamino)-propoxy]-phenyl}-acetic acid

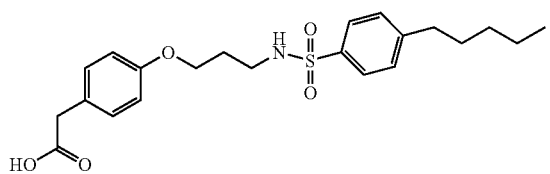

Treatment of 116 in aqueous methanol with 1N aqueos sodium hydroxide afforded the title compound. MS m/e 420; HPLC retention time 3.59 min.

Example 122

N-[3-(1H-Indol-3-ylmethyl)-phenyl]4-pentyl-benzenesulfonamide

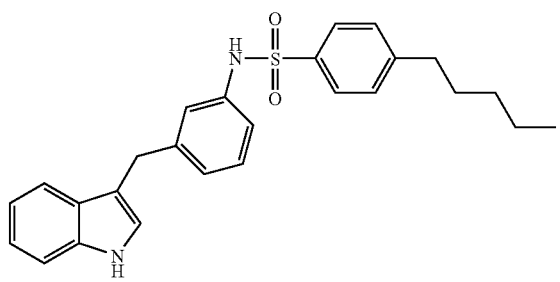

A. 3-(3-Nitro-benzyl)-1H-indole

A mixture of 1H-indole (1.172 g, 10 mmol), 3-nitrobenzyl bromide (2.38 g, 11 mmol) and silver(I) oxide (2.80 g, 12.1 mmol) in 50 ml dioxane was refluxed for 5 h. The mixture was then filtered through celite and concentrated. Chromatography on silica gel using hexane:EtOAc provided 122A as a brown solid.

B. 3-(1H-Indol-3-ylmethyl)-phenylamine 122A (1.36 g, 5.39 mmol) and tin(II) chloride dihydrate (9.73 g, 43.12 mmol) in 150 ml EtOAc were refluxed for 6 h. The mixture was then cooled to room temperature and the pH adjusted to 7 using aqueous sodium bicarbonate. The mixture was then filtered through celite and extracted with EtOAc. The organic extract was washed with brine, dried and concentrated to afford 1.05 g of 122B as a colorless gum, which was used in the next step without purification.

C. N-[3-(1H-Indol-3-ylmethyl)-phenyl]4-pentyl-benzenesulfonamide

A mixture of 122B (87 mg, 0.39 mmol) and 4-n-pentyl-benzenesulphonyl chloride (74 mg, 0.3 mmol) and Et3N (101.2 mg, 0.139 ml, 1.0 mmol) and DMAP (7.3 mg, 0.078 mmol) in 4 ml CH2Cl2 was stirred at room temperature overnight. The mixture was diluted with EtOH, washed with 1% HCl, H2O, brine, dried and concentrated. Chromatography on silica gel using hexane/EtOAc 6:1 provided the title compound as yellow gum. MS m/e 433; HPLC retention time 3.94 min $^1$H NMR: 0.88 (3H, tr, J=7 Hz), 1.29 (m, 4H), 1.65 (m, 2H), 2.57 (m, 2H), 4.00 (s, 2H), 6.69-7.99 (m, 14).

Example 123

N-[2-(1H-Indol-3-ylmethyl)-benzyl]-4-pentyl-benzenesulfonamide

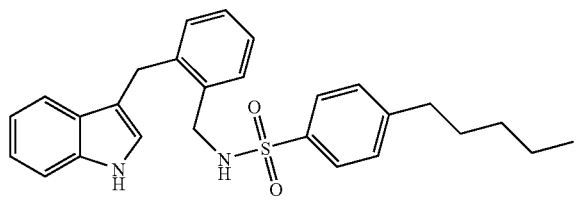

MS m/e 447; HPLC retention time 4.06 min

Example 124

N-[3-(1H-Indol-3-ylmethyl)-benzyl]-4-pentyl-benzenesulfonamide

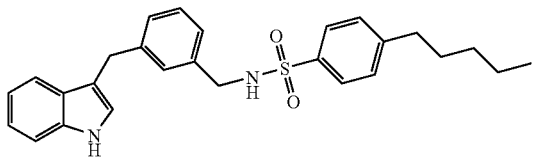

MS m/e 447; HPLC retention time 4.04 min.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound selected from N-[2-(1H-Indol-3-yl)-ethyl]-4-pentyl-benzenesulfonamide; N-[2-(1H-Indol-3-yl)-ethyl]-3-methyl-benzenesulfonamide; N-[2-(1H-Indol-3-yl)-ethyl]-4-fluoro-benzenesulfonamide; N-[2-(1H-indol-3-yl)-ethyl]-2-fluoro-benzenesulfonamide; N-[2-(1H-Indol-3-yl)-ethyl]-3-fluoro-benzenesulfonamide; N-[2-(1H-Indol-3-yl)-ethyl]-4-cyano-benzenesulfonamide; N-[2-(1H-Indol-3-yl)-ethyl]-3-cyano-benzenesulfonamide; N-[2-(1H-Indol-3-yl)-ethyl]-2,5-dimethyl-benzenesulfonamide; N-[2-(1H-Indol-3-yl)-ethyl]-4-ethyl-benzenesulfonamide; N-[2-(1H-Indol-3-yl)-ethyl]-2-methyl-5-fluoro-benzenesulfonamide; N-[2-(1H-Indol-3-yl)-ethyl]-2-chloro-benzenesulfonamide; N-[2-(1H-Indol-3-yl)-ethyl]-3-chloro-benzenesulfonamide; N-[2-(1H-Indol-3-yl)-ethyl]-2,4-difluoro-benzenesulfonamide; N-[2-(1H-Indol-3-yl)-ethyl]-4-propyl-benzenesulfonamide; N-[2-(1H-Indol-3-yl)-ethyl]-4-isopropyl-benzenesulfonamide; N-[2-(1H-Indol-3-yl)-ethyl]-2-methoxy-5-methyl-benzenesulfonamide; N-[2-(1H-Indol-3-yl)-ethyl]-2-nitro-benzenesulfonamide; N-[2-(1H-Indol-3-yl)-ethyl]-3-nitro-benzenesulfonamide; N-[2-(1H-Indol-3-yl)-ethyl]-2-chloro-6-methyl-benzenesulfonamide; N-[2-(1H-Indol-3-yl)-ethyl]-2-methyl-3-chlorol-benzenesulfonamide; N-[2-(1H-Indol-3-yl)-ethyl]-3-chloro-4-methyl-benzenesulfonamide; N-[2-(1H-Indol-3-yl)-ethyl]-3-chloro-4-fluoro-benzenesulfonamide; N-[2-(1H-Indol-3-yl)-ethyl]-2-chloro-4-fluoro-benzenesulfonamide; N-[2-(1H-Indol-3-yl)-ethyl]-2,3,4-trifluoro-benzenesulfonamide; N-[2-(1H-Indol-3-yl)-ethyl]-4-tert-butyl-benzenesulfonamide; N-[2-(1H-Indol-3-yl)-ethyl]-4-butyl-benzenesulfonamide; 2-[2-(1H-Indol-3-yl)-ethylsulfamoyl]-benzoic acid methyl ester; N-[2-(1H-Indol-3-yl)-ethyl]-2-methyl-5-nitro-benzenesulfonamide; N-[2-(1H-Indol-3-yl)-ethyl]-4-methyl-3-nitro-benzenesulfonamide; N-[2-(1H-Indol-3-yl)-ethyl]-2,5-dimethoxy-benzenesulfonamide; N-[2-(1H-Indol-3-yl)-ethyl]-3,4-dimethoxy-benzenesulfonamide; 4-Chloro-N-[2-(1H-indol-3-yl)-ethyl]-2,5-dimethyl-benzenesulfonamide; N-[2-(1H-Indol-3-yl)-ethyl]-3-chloro-6-methoxy-benzenesulfonamide; N-[2-(1H-Indol-3-yl)-ethyl]-2-trifluoromethyl-benzenesulfonamide; N-[2-(1H-Indol-3-yl)-ethyl]-3,4-dichloro-benzenesulfonamide; N-[2-(1H-Indol-3-yl)-ethyl]-2,3-dichloro-benzenesulfonamide; 4-(1,1-Dimethyl-propyl)-N-[2-(1H-indol-3-yl)-ethyl]-benzenesulfonamide; 4-Butoxy-N-[2-(1H-indol-3-yl)-ethyl]-benzenesulfonamide; Biphenyl-4-sulfonic acid [2-(1H-indol-3-yl)-ethyl]-amide; N-[2-(1H-Indol-3-yl)-ethyl]-2-methanesulfonyl-benzenesulfonamide; N-[2-(1H-indol-3-yl)-ethyl]-4-bromo-benzenesulfonamide; N-[2-(1H-Indol-3-yl)-ethyl]-2-bromo-benzenesulfonamide; N-[2-(1H-Indol-3-yl)-ethyl]-3-bromo-benzenesulfonamide; N-[2-(1H-Indol-3-yl)-ethyl]-4-chloro-3-nitro-benzenesulfonamide; N-[2-(1H-Indol-3-yl)-ethyl]-2,4-dichloro-5-methyl-benzenesulfonamide; N-[2-(1H-Indol-3-yl)-ethyl]-2,4-dichloro-6-methyl-benzenesulfonamide; N-[2-(1H-Indol-3-yl)-ethyl]-4-trifluoromethoxy-benzenesulfonamide; N-[2-(1H-Indol-3-yl)-ethyl]-2-trifluoromethoxy-benzenesulfonamide; Dibenzofuran-2-sulfonic acid [2-(1H-indol-3-yl)-ethyl]-amide; N-{2-Chloro-4-[2-(1H-indol-3-yl)-ethylsulfamoyl]-phenyl}-acetamide; 4-Bromo-N-[2-(1H-indol-3-yl)-ethyl]-2-methyl-benzenesulfonamide; 2-Chloro-N-[2-(1H-indol-3-yl)-ethyl]-5-trifluoromethyl-benzenesulfonamide; 2-Chloro-N-[2-(1H-indol-3-yl)-ethyl]-4-trifluoromethyl-benzenesulfonamide; 2,4,5-Trichloro-N-[2-(1H-indol-3-yl)-ethyl]-benzenesulfonamide; 2,4,6-Trichloro-N-[2-(1H-indol-3-yl)-ethyl]-benzenesulfonamide; 4-Bromo-2-ethyl-N-[2-(1H-indol-3-yl)-ethyl]-benzenesulfonamide; 5-Bromo-N-[2-(1H-indol-3-yl)-ethyl]-2-methoxy-benzenesulfonamide; N-[2-(1H-Indol-3-yl)-ethyl]-3,5-bis-trifluoromethyl-benzenesulfonamide; 4-(3-Chloro-2-cyano-phenoxy)-N-[2-(1H-indol-3-yl)-ethyl]-benzenesulfonamide; 4-(2-Chloro-6-nitro-phenoxy)-N-[2-(1H-indol-3-yl)-ethyl]-benzenesulfonamide; N-[2-(1H-Indol-3-yl)-ethyl]-2,5-bis-(2,2,2-trifluoro-ethoxy)-benzenesulfonamide; N-[3-(1H-Indol-3-yl)-propyl]-4-pentyl-benzenesulfonamide; N-[3-(1H-Indol-3-yl)-butyl]-4-pentyl-benzenesulfonamide; 4'-Methyl-biphenyl-4-sulfonic acid [2-(1H-indol-3-yl)-ethyl]-amide; 3'-Methyl-biphenyl-4-sulfonic acid [2-(1H-indol-3-yl)-ethyl]-amide; 2'-Methyl-biphenyl-4-sulfonic acid [2-(1H-indol-3-yl)-ethyl]-amide; 4'-Ethyl-biphenyl-4-sulfonic acid [2-(1H-indol-3-yl)-ethyl]-amide; 4'-tert-Butyl-biphenyl-4-sulfonic acid [2-(1H-indol-3-yl)-ethyl]-amide; 4'-Trifluoromethyl-biphenyl-4-sulfonic acid [2-(1H-indol-3-yl)-ethyl]-amide; 4'-Methoxy-biphenyl-4-sulfonic acid [2-(1H-indol-3-yl)-ethyl]-amide; 4'-Isopropyl-biphenyl-4-sulfonic acid [2-(1H-indol-3-yl)-ethyl]-amide; 4'-Methylsulfanyl-biphenyl-4-sulfonic acid [2-(1H-indol-3-yl)-ethyl]-amide; N-[2-(1H-Indol-3-yl)-ethyl]-4-thiophen-2-yl-benzenesulfonamide; N-[2-(1H-Indol-3-yl)-ethyl]-4-thiophen-3-yl-benzenesulfonamide; 4-Benzofuran-2-yl-N-[2-(1H-indol-3-yl)-ethyl]-benzenesulfonamide; 4'-Isobutyl-biphenyl-4-sulfonic acid [2-(1H-indol-3-yl)-ethyl]-amide; 4'-(3-Methyl-butyl)-biphenyl-4-sulfonic acid [2-(1H-indol-3-yl)-ethyl]-amide; 4'-n-Butyl-biphenyl-4-sulfonic acid [2-(1H-indol-3-yl)-ethyl]-amide; 4'-Cyclopentylmethyl-biphenyl-4-sulfonic acid [2-(1H-indol-3-yl)-ethyl]-amide; 4'-Formyl-biphenyl-4-sulfonic acid [2-(1H-indol-3-yl)-ethyl]-amide; 3',4'-Dimethyl-biphenyl-4-sulfonic acid [2-(1H-indol-3-yl)-ethyl]-amide; 3'-Trifluoromethyl-biphenyl-4-sulfonic acid [2-(1H-indol-3-yl)-ethyl]-amide; 3'-Chloro-biphenyl-4-sulfonic acid [2-(1H-indol-3-yl)-ethyl]-amide; 3',5'-Ditrifluoromethyl-biphenyl-4-sulfonic acid [2-(1H-indol-3-yl)-ethyl]-amide; N-{4'-[2-(1H-Indol-3-yl)-ethylsulfamoyl]-biphenyl-3-yl}-acetamide; 3'-Methoxy-biphenyl-4-sulfonic acid [2-(1H-indol-3-yl)-ethyl]-amide; Biphenyl-3-sulfonic acid [2-(1H-indol-3-yl)-ethyl]-amide; 4'-Isopropyl-biphenyl-3-sulfonic acid [2-(1H-indol-3-yl)-ethyl]-amide; 4'-[2-(1H-Indol-3-yl)-ethylsulfamoyl]-biphenyl-4-carboxylic acid; Biphenyl-3-sulfonic acid [3-(1H-indol-3-yl)-propyl]-amide; 2'-Chloro-biphenyl-3-sulfonic acid [3-(1H-indol-3-yl)-propyl]-amide; 4'-Isopropyl-biphenyl-3-sulfonic acid [3-(1H-indol-3-yl)-propyl]-amide; 4'-Chloro-biphenyl-3-sulfonic acid [3-(1H-indol-3-yl)-propyl]-amide; 3'-Fluoro-biphenyl-3-sulfonic acid [3-(1H-indol-3-yl)-propyl]-amide; Biphenyl-4-sulfonic acid [3-(1H-indol-3-yl)-propyl]-amide; 4'-Isopropyl-biphenyl-4-sulfonic acid [3-(1H-indol-3-yl)-propyl]-amide; 4'-Ethyl-biphenyl-4-sulfonic acid [3-(1H-indol-3-yl)-propyl]-amide; 4-[2-(1H-indol-3-yl)-ethylsulfamoyl]-benzoic acid; 4-[2-(1H-Indol-3-yl)-ethylsulfamoyl]-N-phenyl-benzamide; N-Benzyl-4-[2-(1H-indol-3-yl)-ethylsulfamoyl]-benzamide; N-[2-(1H-Indol-3-yl)-ethyl]-4-phenoxymethyl-benzenesulfonamide 3-{4-[3-(4-Pentyl-benzenesulfonylamino)-propoxy]-phenyl}-propionic acid methyl ester; N-[3-(2-Amino-phenoxy)-propyl]-4-pentyl-benzenesulfonamide; {4-[3-(4-Pentyl-benzenesulfonylamino)-propoxy]-phenyl}-acetic acid methyl ester; 3-{4-[3-(4-Pentyl-benzenesulfonylamino)-propoxy]-phenyl}-propionic acid methyl ester; {4-[2-(4-Pentyl-benzenesulfonylamino)-ethoxy]-phenyl}-acetic acid methyl ester; 3-{3-[3-(4-Pentyl-benzenesulfonylamino)-propoxy]-phenyl}-propionic acid methyl ester; N-Methyl-3-{4-[3-(4-pentyl-benzenesulfonylamino)-propoxy]-phenyl}-propionamide; N-[3-(4-Butyl-phenoxy)-propyl]-4-pentyl-benzenesulfonamide; 3-{4-[3-(4-Pentyl-benzenesulfonylamino)-propoxy]-phenyl}-propionic acid; {4-[3-(4-Pentyl-benzenesulfonylamino)-propoxy]-phenyl}-acetic acid; N-[3-(1H-indol-3-ylmethyl)-phenyl]-4-pentyl-benzenesulfonamide; N-[2-(1H-Indol-3-ylmethyl)-benzyl]-4-pentyl-benzenesulfonamide; and N-[3-(1H-Indol-3-ylmethyl)-benzyl]-4-pentyl-benzenesulfonamide.

2. A pharmaceutical composition, comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,754,755 B2
APPLICATION NO. : 11/231729
DATED : July 13, 2010
INVENTOR(S) : Natesan Murugesan et al.

It is certified that error appears in the above-identified patent and that said Letters Patent is hereby corrected as shown below:

On the Title Page, item [56] col. 1, (Other Publications), line 2, delete "Benzoyltrytamines" and insert -- Benzoyltryptamines --, therefor.

On the Title Page, item [56] col. 2, (Other Publications), line 26, delete "Inosito" and insert -- Inositol --, therefor.

Claim 1, col. 61, line 13, delete "benzenesulfonamide" and insert -- benzenesulfonamide; --, therefor.

Signed and Sealed this
Third Day of May, 2011

David J. Kappos
*Director of the United States Patent and Trademark Office*